(12) United States Patent
Sullivan et al.

(10) Patent No.: US 9,545,211 B2
(45) Date of Patent: *Jan. 17, 2017

(54) SYSTEM AND METHOD FOR ELECTROCARDIOGRAM ANALYSIS AND OPTIMIZATION OF CARDIOPULMONARY RESUSCITATION AND THERAPY DELIVERY

(71) Applicant: PHYSIO-CONTROL, INC., Redmond, WA (US)

(72) Inventors: Joseph L. Sullivan, Kirkland, WA (US); Ronald Eugene Stickney, Edmonds, WA (US); Robert G. Walker, Seattle, WA (US); Daniel Piraino, Seattle, WA (US); Isabelle Banville, Newcastle, WA (US); Fred Chapman, Newcastle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/656,666

(22) Filed: Mar. 12, 2015

(65) Prior Publication Data

US 2015/0297107 A1 Oct. 22, 2015

Related U.S. Application Data

(63) Continuation-in-part of application No. 14/558,610, filed on Dec. 2, 2014, now Pat. No. 9,283,400, which
(Continued)

(51) Int. Cl.
*A61B 5/04* (2006.01)
*A61N 1/39* (2006.01)
(Continued)

(52) U.S. Cl.
CPC ......... *A61B 5/04017* (2013.01); *A61H 31/005* (2013.01); *A61H 31/006* (2013.01);
(Continued)

(58) Field of Classification Search
CPC ... A61B 5/046; A61B 5/04017; A61B 5/7217; A61B 5/4836; A61B 5/0402; A61B 5/044; A61B 5/7207; A61B 5/721; A61B 5/7475; A61N 1/3925; A61N 1/39; A61N 1/3987; A61N 1/3993
See application file for complete search history.

(56) References Cited

U.S. PATENT DOCUMENTS 5,687,735 A    11/1997   Forbes et al.
6,752,771 B2 *   6/2004   Rothman et al. ............... 601/44
(Continued)

FOREIGN PATENT DOCUMENTS

WO    2009071128    6/2009

OTHER PUBLICATIONS

Dotsinsky, I., Suppression of AC railway power-line interference in ECG signals recorded by public access defibrillators, BioMedical Engineering Online (2005) 4:65.
(Continued)

*Primary Examiner* — Rex R Holmes
(74) *Attorney, Agent, or Firm* — Marger Johnson

(57) ABSTRACT

The system and method provide for electrocardiogram analysis and optimization of patient-customized cardiopulmonary resuscitation and therapy delivery. An external medical device includes a housing and a processor within the housing. The processor can be configured to receive an input signal for a patient receiving chest compressions and to select at least one filter mechanism and to apply the filter mechanism to the signal to at least substantially remove chest compression artifacts from the signal. A real time
(Continued)

DEFIBRILLATION SCENE dynamic analysis of a cardiac rhythm is applied to adjust and integrate CPR prompting of a medical device. Real-time cardiac rhythm quality is facilitated using a rhythm assessment meter.

21 Claims, 24 Drawing Sheets

Related U.S. Application Data is a continuation of application No. 13/836,062, filed on Mar. 15, 2013, now Pat. No. 8,903,498, which is a continuation-in-part of application No. 13/676,593, filed on Nov. 14, 2012, now Pat. No. 9,084,545.

(60) Provisional application No. 61/952,039, filed on Mar. 12, 2014, provisional application No. 61/952,074, filed on Mar. 12, 2014, provisional application No. 61/616,660, filed on Mar. 28, 2012, provisional application No. 61/616,847, filed on Mar. 28, 2012, provisional application No. 61/616,973, filed on Mar. 28, 2012, provisional application No. 61/616,874, filed on Mar. 28, 2012, provisional application No. 61/616,372, filed on Mar. 27, 2012, provisional application No. 61/616,727, filed on Mar. 28, 2012, provisional application No. 61/642,407, filed on May 3, 2012.

(51) Int. Cl.
*A61H 31/00* (2006.01)
*A61B 5/044* (2006.01)
*A61B 5/00* (2006.01)
*A61B 5/046* (2006.01)

(52) U.S. Cl.
CPC ......... *A61N 1/3925* (2013.01); *A61N 1/3987* (2013.01); *A61N 1/3993* (2013.01); *A61B 5/044* (2013.01); *A61B 5/046* (2013.01); *A61B 5/04014* (2013.01); *A61B 5/725* (2013.01); *A61B 5/7207* (2013.01); *A61B 5/7217* (2013.01); *A61H 2201/5007* (2013.01); *A61H 2201/5043* (2013.01); *A61H 2201/5097* (2013.01); *A61H 2230/045* (2013.01); *A61H 2230/206* (2013.01); *A61H 2230/208* (2013.01); *A61H 2230/305* (2013.01)

(56) References Cited

U.S. PATENT DOCUMENTS

| 7,039,457 | B2 | 5/2006 | Young et al. |
|---|---|---|---|
| 7,220,235 | B2 | 5/2007 | Geheb et al. |
| 7,565,194 | B2 | 7/2009 | Tan et al. |
| 7,567,837 | B2 | 7/2009 | Weil et al. |
| 7,650,181 | B2 | 1/2010 | Freeman et al. |
| 7,831,299 | B2 | 11/2010 | Tan et al. |
| 2002/0165471 | A1 | 11/2002 | Halperin et al. |
| 2005/0101889 | A1 | 5/2005 | Freeman et al. |
| 2005/0137628 | A1 | 6/2005 | Young et al. |
| 2005/0256415 | A1 | 11/2005 | Tan et al. |
| 2006/0025824 | A1 | 2/2006 | Freeman et al. |
| 2006/0149157 | A1 | 7/2006 | Weil et al. |
| 2006/0235320 | A1 | 10/2006 | Tan et al. |
| 2006/0258927 | A1 | 11/2006 | Edgar et al. |
| 2007/0100379 | A1 | 5/2007 | Tan et al. |
| 2007/0162076 | A1 | 7/2007 | Tan et al. |
| 2010/0076510 | A1 | 3/2010 | Lyster |
| 2011/0034816 | A1 | 2/2011 | Tan et al. |
| 2011/0105930 | A1 | 5/2011 | Thiagarajan et al. |
| 2011/0202100 | A1 | 8/2011 | Tan et al. |
| 2011/0202101 | A1 | 8/2011 | Tan et al. |
| 2012/0010543 | A1 | 1/2012 | Johnson et al. |
| 2012/0016279 | A1 | 1/2012 | Banville et al. |
| 2012/0157865 | A1 | 6/2012 | Stein et al. |
| 2013/0184600 | A1* | 7/2013 | Tan et al. ............ 600/518 |
| 2014/0088374 | A1 | 3/2014 | Sullivan et al. |

OTHER PUBLICATIONS

Dotsinsky, I. et al., Fast electrocardiogram amplifier recovery after a defibrillation shock, Bioautomation (2005) 2:76-84.

Ruiz, J. et al., Cardiopulmonary resuscitation artefact suppression using a Kalman filter and the frequency of chest compressions as the reference signal, Resuscitation 81 (2010) 1087-1094.

Aramendi et al., Detection of ventricular fibrillation in the presence of cardiopulmonary resuscitation artefacts, Resuscitation (2007) 75: 115-123.

Lee, B. et al., Adaptive comb filtering for motion artifact reduction from PPG with a structure of adaptive lattice IIR notch filter, 33rd Annual International Conference of the IEEE EMBS, Boston, MA, Aug. 30-Sep. 3, 2011, 4 pages.

Granegger, M. et al., Use of independent component analysis for reducing CPR artefacts in human emergency ECGs, Resuscitation (2011) 82: 79-84.

Irusta U. et al., A least mean-square filter for the estimation of the cardiopulmonary resuscitation artifact based on the frequency of the compressions, IEEE Trans Biomed Eng (2009) 56:21052-62.

Ruiz de Gauna et al., A method to remove CPR artefacts from human ECG using only the recorded ECG, Resuscitation (2008) 76, 271-278.

Aramendi et al., Suppression of the cardiopulmonary resuscitation artefacts using the instantaneous chest compressions rate extracted from the thoracic impedance, Resuscitation 83 (2012) 692-698.

Berger et al., Rhythm discrimination during uninterrupted CPR using motion artifact reduction system, Resuscitation (2007) 75, 145-152.

Aramendi, et al., "A simple effective filtering method for removing CPR cause artefacts from surface ECG signals"; Computers in Cardiology; 2005; pp. 547-550.

International Search Report and Written Opinion; Patent Cooperation Treaty; Oct. 1, 2013; 22 pages; PCT/US2013/039555, European Patent Office.

* cited by examiner

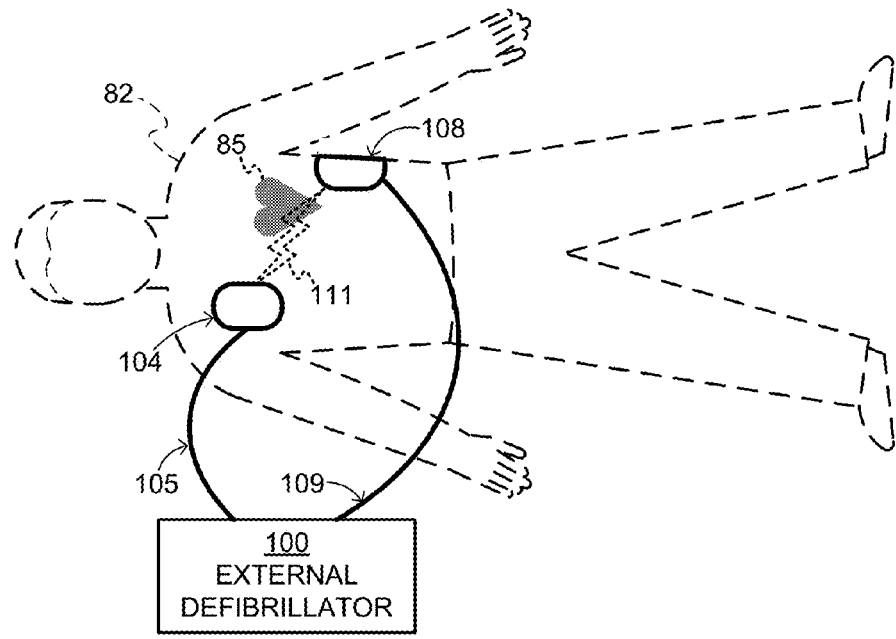
FIG. 1   *DEFIBRILLATION SCENE*
| TYPE OF EXTERNAL DEFIBRILLATOR | INTENDED TO BE USED BY PERSONS: ||
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2   *TWO MAIN TYPES OF EXTERNAL DEFIBRILLATORS*

COMPONENTS OF EXTERNAL DEFIBRILLATOR

*FAST FOURIER TRANSFORM OF ECG SIGNAL FROM ASYSTOLIC PATIENT RECEIVING CHEST COMPRESSIONS FROM CONVENTIONAL MECHANICAL CPR DEVICE*

FIG. 6 *FAST FOURIER TRANSFORM OF ECG SIGNAL FROM ASYSTOLIC PATIENT RECEIVING CHEST COMPRESSIONS FROM MECHANICAL CPR DEVICE HAVING PRECISE FREQUENCY CONTROL*

*FREQUENCY RESPONSE OF A COMB FILTER TO REMOVE CHEST COMPRESSION ARTIFACTS FROM ECG SIGNAL*

FIG. 8  *FREQUENCY RESPONSE OF AN INVERSE COMB FILTER TO REMOVE CHEST COMPRESSION ARTIFACTS FROM ECG SIGNAL*

SAMPLE PATIENT ECG DATA

FIG. 10A SAMPLE ECG SIGNAL HAVING QRS COMPLEXES AND NO CHEST COMPRESSION ARTIFACTS

FIG. 10B SAMPLE ECG SIGNAL HAVING QRS COMPLEXES AND CHEST COMPRESSION ARTIFACTS WITH NO FILTERING

FIG. 10C SAMPLE ECG SIGNAL HAVING QRS COMPLEXES AND CHEST COMPRESSION ARTIFACTS WITH FILTER APPLIED

FIG. 11A SAMPLE ECG SIGNAL HAVING NO QRS COMPLEXES AND NO CHEST COMPRESSION ARTIFACTS

FIG. 11B SAMPLE ECG SIGNAL HAVING NO QRS COMPLEXES AND CHEST COMPRESSION ARTIFACTS WITH NO FILTERING

FIG. 11C SAMPLE ECG SIGNAL HAVING NO QRS COMPLEXES AND CHEST COMPRESSION ARTIFACTS WITH FILTER APPLIED

FIG. 12A SAMPLE VF SIGNAL HAVING NO CHEST COMPRESSION ARTIFACTS

FIG. 12B SAMPLE VF SIGNAL HAVING CHEST COMPRESSION ARTIFACTS WITH NO FILTERING

FIG. 12C SAMPLE VF SIGNAL HAVING CHEST COMPRESSION ARTIFACTS WITH FILTER APPLIED

FIG. 13 — METHODS ACCORDING TO EMBODIMENTS

METHODS ACCORDING TO EMBODIMENTS

FIG. 15  METHODS ACCORDING TO EMBODIMENTS

| Shock Index Value | Probability of VF | Interpretation | Recommended action |
|---|---|---|---|
| -5 | 1% | Definitely non-shockable | Continue CPR |
| -2.5 | 7.5% | Non-shockable | |
| -1 | 26% | Probably non-shockable | Stop CPR to assess rhythm every 2 minutes |
| 0 | 50% | Don't know | |
| 1 | 73% | Probably shockable | |
| 2.5 | 92% | Shockable | Shock now |
| 5 | 99% | Definitely shockable | |

*PERIODIC MODE METHOD ACCORDING TO EMBODIMENTS*

CONTINUOUS CPR MODE METHOD ACCORDING TO EMBODIMENTS

MINIMUM CPR MODE METHOD
ACCORDING TO
EMBODIMENTS

SYSTEM AND METHOD FOR ELECTROCARDIOGRAM ANALYSIS AND OPTIMIZATION OF CARDIOPULMONARY RESUSCITATION AND THERAPY DELIVERY

CROSS-REFERENCE TO RELATED APPLICATIONS

This application claims the benefit of U.S. Provisional Application No. 61/952,039 entitled "Pause Coordination for CPR Artifact Filtering" and U.S. Provisional Application No. 61/952,074 entitled "Compression Rate Assessment for Accurate Comb Filtering", and further this application is a continuation-in-part of U.S. patent application Ser. No. 14/558,610 entitled "System and Method for Electrocardiogram Analysis and Optimization of Cardiopulmonary Resuscitation and Therapy Delivery", which issued Mar. 15, 2016 as U.S. Pat. No. 9,283,400 and is a continuation of U.S. patent application Ser. No. 13/836,062 entitled "System and Method for Electrocardiogram Analysis and Optimization of Cardiopulmonary Resuscitation and Therapy Delivery", which issued Dec. 2, 2014 as U.S. Pat. No. 8,903,498 and is a continuation-in-part of U.S. patent application Ser. No. 13/676,593, entitled "Filter Mechanism for Removing ECG Artifact from Mechanical Chest Compressions," filed Dec. 13, 2012, which issued Jul. 21, 2015 as U.S. Pat. No. 9,084,545 and claims the benefit of: U.S. Provisional Application No. 61/616,874 entitled "Visual Rhythm Assessment Meter," filed Mar. 28, 2012; U.S. Provisional Application No. 61/616,727, entitled "ECG Frequency Analysis during CPR," filed Mar. 28, 2012; U.S. Provisional Application No. 61/616,973 entitled "An Analysis during CPR Algorithm Utilizing Shock History," filed Mar. 28, 2012; U.S. Provisional Application No. 2061/616,660 entitled "Guiding Therapy with Real-Time VF Quality Measurement," filed Mar. 28, 2012; U.S. Provisional Application No. 61/616,372 entitled "AED Operation Dependent on Previous Analysis Results," filed Mar. 27, 2012; and U.S. Provisional Application No. 61/616,847 entitled "Method of Integrating Cardiac Rhythm Analysis during CPR into an AED Algorithm" filed Mar. 28, 2012, all of which are hereby incorporated by reference herein in their entirety.

FIELD

This invention generally relates to medical devices, such as external defibrillators and chest compression devices.

BACKGROUND

In normal operation, the heart pumps blood through the various parts of the body in a well-orchestrated fashion. The chambers of the heart contract and expand in a periodic and coordinated harmony, causing the blood to be pumped regularly. In humans, the right atrium sends deoxygenated blood into the right ventricle. The right ventricle pumps the blood to the lungs, where the blood becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. The sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated promptly, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, the person will die soon, e.g. within ten minutes.

Ventricular Fibrillation can often be reversed using a life-saving device called a defibrillator. A defibrillator, if applied properly, can administer an electrical shock to the heart. The shock may terminate the VF, thus. giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel. For individuals who are not an ICD candidates but still in need of monitoring, a portable defibrillator that can be worn by the individual at risk can be used.

Regardless, VF can occur unpredictably, even to a person who is not considered at risk and has not been monitored. As such, VF can be experienced by many people who lack the benefit of ICD or wearable therapy. When VF occurs to a person, every minute counts. During VF, if the blood is not flowing to the brain, heart, lungs, and other organs, the person's condition deteriorates rapidly. If resuscitation attempts are to be successful, blood flow must be restored as quickly as possible. Cardiopulmonary Resuscitation (CPR) is one method of forcing blood flow in a person experiencing cardiac arrest. AEDs analyze the patient's electrocardiogram (ECG) to decide whether a patient needs a shock. External defibrillators may also prompt the rescuer to provide chest compressions, rescue breathing, and/or shocks based on established protocols.

In some cases, it is recognized that patients benefit greatly from CPR prior to defibrillation. Properly administered CPR provides oxygenated blood to critical organs of a person in cardiac arrest, thereby minimizing the deterioration that would otherwise occur. For patients with an extended downtime, survival rates are higher if CPR is administered prior to defibrillation. CPR is often critical for a patient's survival from sudden cardiac arrest and is the primary recommended treatment for some patients with some kinds of non-VF cardiac arrest, such as asystole and pulseless electrical activity (PEA). CPR may be a combination of techniques that include chest compressions to force blood circulation, and rescue breathing to force respiration.

In this race against time for human life, being able to, in real-time, understand the optimal amount, durations, pauses, administration frequency of CPR in combination of shock therapy, as well as how to improve and what to do when the CPR quality is poor, is highly desirable. Being able to monitor and analyze, and customize the CPR and the rhythm at the same time and in real-time, determine when to start with a CPR or a shock first, whether to stop altogether, or continue for a longer than routine/protocol-prescribed period to resuscitate successfully, is highly desirable and highly sought after. However, prior attempts, due to issues largely related to noise artifact, have failed to providing a system and method capable of successful monitoring and analyzing of rhythms, and other physiological signals and parameters, while performing chest compressions.

Furthermore, to-date, the ECG analysis and evaluation at any given point has been held independent of the previous sets of results. Analysis algorithm depends solely on the signal currently being received from the patient. Typically, this signal might be an ECG signal, but it may also include other parameters such as the impedance signal or an accelerometer signal, etc. Administration of CPR follows a protocol in which the number of compressions, pauses for breaths, and the timing of pauses for analysis have been fixed, and often stand independent of the individual patient's history and needs.

Fixed treatment CPR/shock therapy protocol and rigid analysis algorithms are sub-optimal in many situations. The initial rhythm that is presented when the defibrillator is first connected to the patient is a strong predictor of the course of events for that particular patient. Patients who present with the initial rhythm of VF or ventricular tachycardia (VT) have an approximately 50% chance of being in VF or VT on a subsequent analysis. However, in the subset of patients with a non-shockable initial rhythm and with a no-shock result for every subsequent analysis, there is only an approximate 7% chance that they will be in a shockable rhythm on next analysis. This situation is more extreme for Automated External Defibrillator cases than in Advanced Life Support (ALS) care.

Resuscitation researchers have long known that the prognosis for patients with an initial rhythm of asystole is dire. Resuscitation centers are increasingly interested in an approach that tailors the next step in the patient care based on first ECG analysis, AED shock decision. For example, if the first AED decision is "shock advised," AED analysis should be prompted by a device and performed every two minutes. However, if the initial AED decision is "no shock," the remaining AED prompts should not be acted upon (i.e. re-analyzed) and CPR should be performed until ALS care arrives. Whether the initial rhythm is shockable, and whether any subsequent analysis gives a shockable result, are powerful predictors of the patient's condition at any point in time. What is sought is a system and method which can take into account real-time continuous analysis, results, and representation of a rhythm analysis and provide advice as to the next action step or sequence of steps. In addition to "shock" or "no-shock" advice, a representation of a relative shockability recommendation on a scale where "shock" is one end of the scale and "no-shock" the other end of the scale would enable rescuers to optimize shock therapy and CPR at patient-customized frequency and time intervals.

Defibrillator users have a strong desire to be able to analyze an ECG signal and make a shock/no shock decision while chest compressions are being performed. Therefore, what is needed is a system and method which filters noise artifact and enables ECG and CPR patient-customized collaboration, result analysis and evaluation, and optimization of CPR and therapy delivery.

BRIEF SUMMARY

The present description gives instances of devices, systems, software and methods, the use of which may help overcome problems and limitations of the prior art.

When analyzing a relatively noisy data, such as an Electrocardiogram (ECG) during a Cardiopulmonary Resuscitation (CPR), definitive recommendations are not always possible or most helpful. In certain embodiments, an external medical device may include a housing, an energy storage module within the housing for storing an electrical charge, and a defibrillation port for guiding via electrodes the stored electrical charge to a person. The device may also include a processor in the housing configured to receive a signal from a patient receiving chest compressions and apply at least one filter to remove from the signal chest compression artifacts resulting from the chest compressions being delivered to the patient. An advantage over the prior art is that an external medical device in accordance with the disclosed technology can present to a user a cleaner signal than would otherwise be provided in situations where a patient is receiving chest compressions. Also, the device may determine from chest compression artifacts in the patient signal a chest compression signature that corresponds to at least one particular type of chest compression device.

In one embodiment, a real-time analysis of the quality of a cardiac rhythm, such as a quality of a ventricular fibrillation, is continuously and automatically performed during CPR. Based on the analysis, the indication is then presented in real-time, by way of an example, a gauge or a bar graph, a trend line, or a calorimetric scale. The indication may be visual, auditory, tactile, or a combination thereof, etc. The CPR is continued as long as the ventricular fibrillation indicates this course of action. The indication can be presented to a human rescuer or communicated to a mechanical device, which then, automatically responds by adjusting the treatment administered sequence, duration, pauses, etc. An "optimal" amount of CPR is also determined prior to defibrillation. Such approach is patient-tailored and an improvement over performing CPR for a fixed period of time or until a fixed threshold of certainty is reached with respect to CPR/Therapy delivery intervals. If the ventricular fibrillation quality continues to improved, the CPR is continued rather than stopped, per existing protocols.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

DETAILED DESCRIPTION

Figure 3:
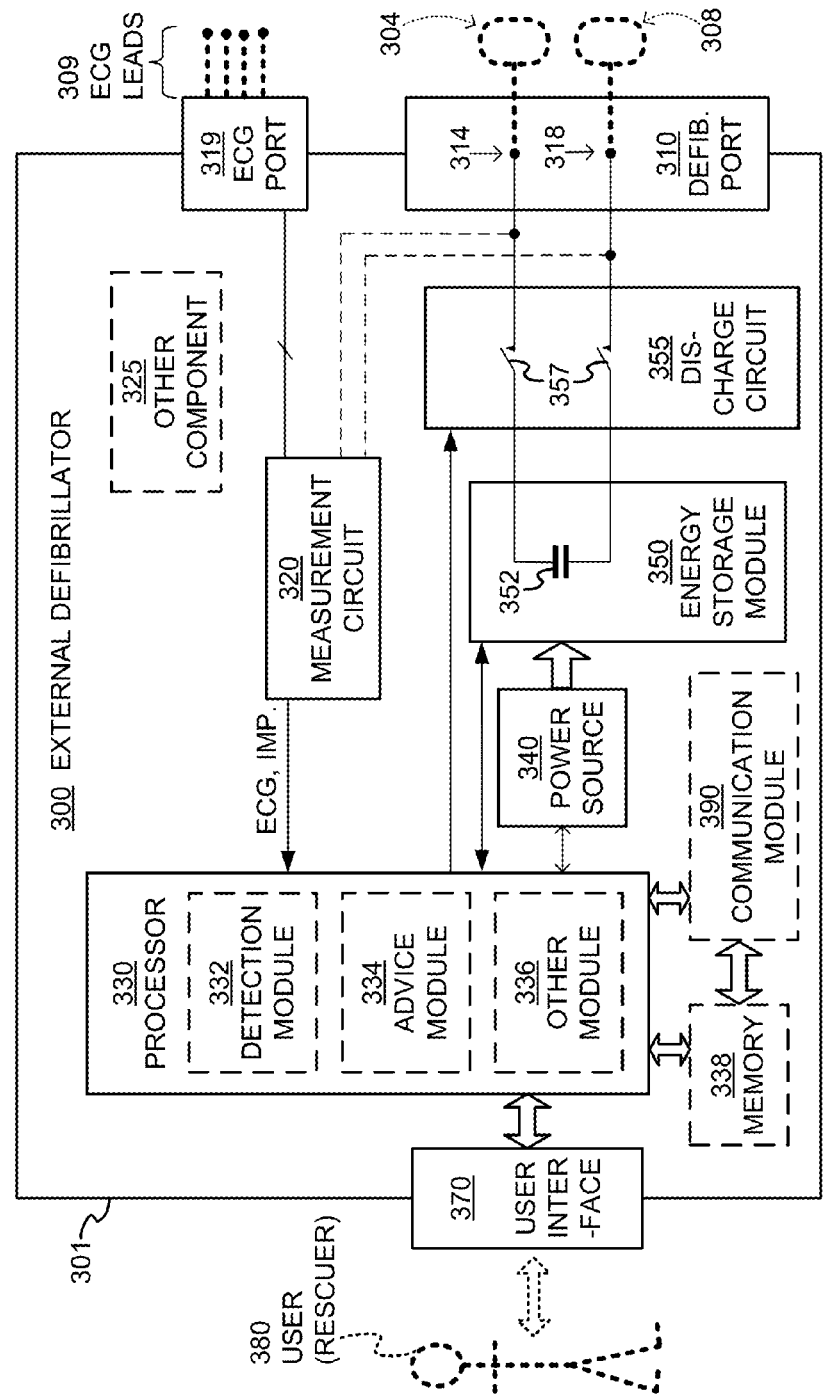
FIG. 3 is a functional block diagram showing components of an external defibrillator, such as the one shown in FIG. 1, which is made according to embodiments.

As has been mentioned, the present description is about medical devices, methods of operating such medical devices, and a programmed processor to control such medical devices for removing chest compression artifacts from an ECG signal for a patient receiving chest compressions and further for analyzing the electrocardiogram for optimization of chest compression and therapy delivery.

Embodiments are now described in more detail.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be, by way of an example, Ventricular Fibrillation (VF).

A portable external defibrillator 100 has been brought close to person 82. The portable external defibrillator can also be a wearable or hybrid defibrillator 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing examples of types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and an other component 325 structured to filter the ECG signal, e.g., apply at least one filter to the signal so as to remove chest compression artifacts resulting from chest compressions being delivered to the person 82.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

A feature of a defibrillator can be CPR-prompting. Prompts are issued to the user, visual or by sound, so that the user can administer CPR. Examples are taught in U.S. Pat. No. 6,334,070 and No. 6,356,785.

System for Filter Mechanism for Removing EGG Artifact from CPR

Figure 4:
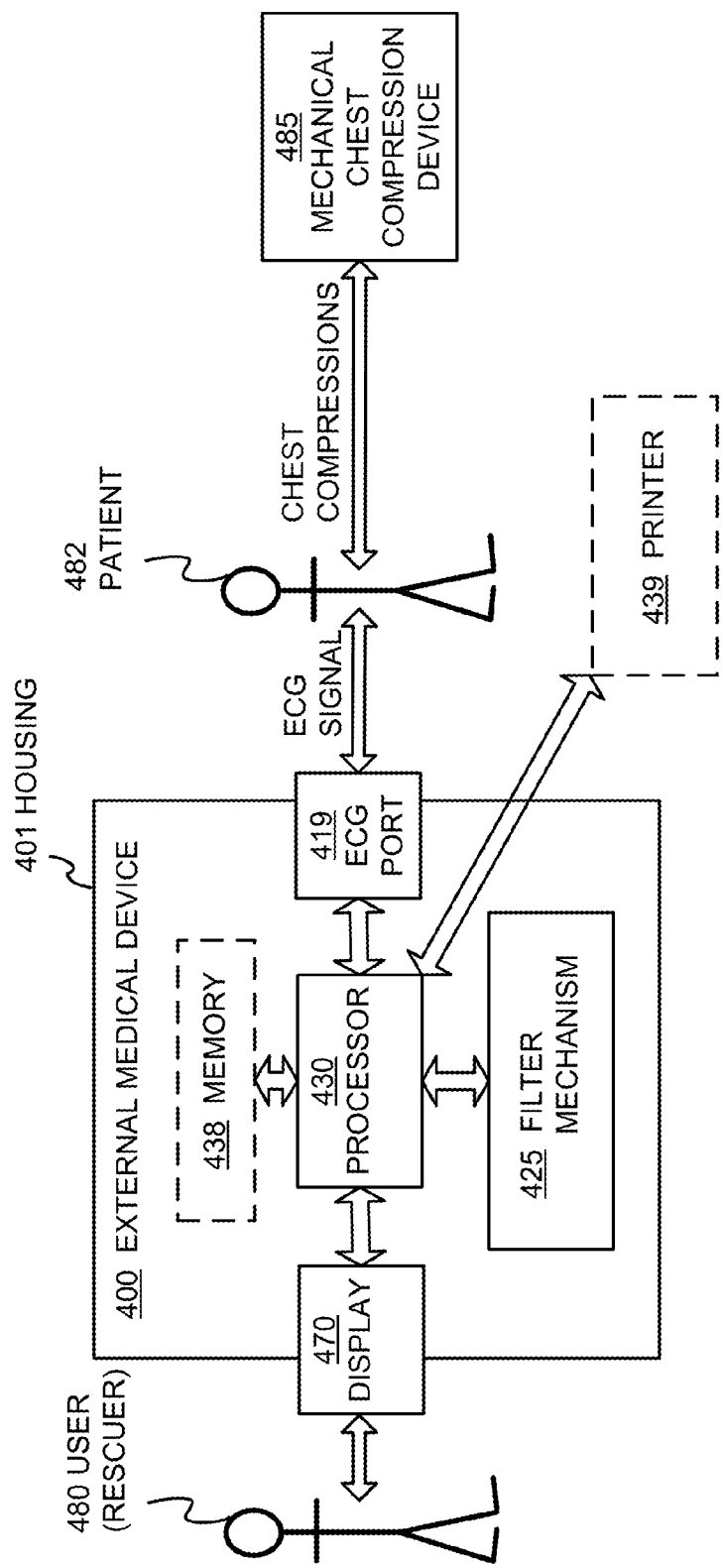
FIG. 4 is a functional block diagram showing components of a patient ECG signal monitoring system according to embodiments.

FIG. 4 is a functional block diagram showing components of a patient ECG signal monitoring system according to embodiments. The system includes an external medical device 400, such as an external defibrillator, having a housing 401, a display 470 in connection with the housing 401, and a processor 430 within the housing 401. One having ordinary skill in the art will recognize that systems according to embodiments generally require no additional sensors or sensor mechanisms than those already provided.

In the example, the system also includes a mechanical chest compression device 485. The mechanical chest compression device 485 may deliver compressions at 100+/−0.01 compressions/minute, which is 1⅔+/−0.00017 Hz. Such precise frequency control is unusual for typical chest compression devices. An ECG signal may thus be corrupted by chest compression artifacts corresponding to chest compressions delivered by the chest compression device 485 to the patient 482. Such artifacts may have an artifact fundamental frequency of 1⅔ Hz, and the artifact signal may also contain harmonics of 1⅔ Hz, which will show up at multiples of 1⅔ Hz, e.g., 3⅓ Hz, 5.0 Hz, and 6⅔ Hz. The spectral content of these frequency components is generally extremely narrow.

The processor 430 may be configured to receive an input signal containing ECG data for a patient 482 receiving chest compressions from the mechanical chest compression device 485. The input signal may be received via an ECG port 419 in connection with the housing 401. In certain embodiments, the processor 430 is further configured to detect the chest compressions being delivered to the patient 482.

The processor 430 may be further configured to select at least one filter mechanism 425, the mechanical chest compression device 485 having a chest compression frequency f. The mechanical chest compression device 485 may provide an indication of the frequency f to the processor 430.

In certain embodiments, the at least one filter mechanism 425 comprises a comb filter. The comb filter may be non-adaptive. In other embodiments, the at least one filter mechanism 425 comprises a plurality of notch filters. Each of the notch filters may be non-adaptive. One having ordinary skill in the art will readily recognize that various other filter mechanisms may be used in addition to or in place of a comb filter or notch filters.

Certain conventional CPR artifact filters may be adaptive in nature. As used herein, an adaptive filter generally refers to a filter whose transfer function is dependent on the input signal. An adaptive filter may adjust its filter coefficients, center frequency, rolloff, notch width, Q, or other characteristic based on the input signal. Non-adaptive filters according to embodiments generally use predetermined coefficients that may precisely set the transfer function independent of the input signal.

It is possible that a device incorporating this invention may include multiple non-adaptive filters. The appropriate filter may be selected based on input signal characteristics, such as the frequency content of the ECG signal or impedance signal. Alternatively, the appropriate filter may be selected by communication with the mechanical chest compression device, or through a user input selection.

In certain embodiments, the selecting of the at least one filter mechanism 425 is performed responsive to an identification of the mechanical chest compression device 485 being used to deliver the chest compressions to the patient 482. Alternatively or in addition thereto, the processor 430 may be configured to select the at least one filter mechanism 425 responsive to input received from the mechanical chest compression device 485 delivering the chest compressions to the patient 482. In certain embodiments, the processor 430 may be configured to select the at least one filter mechanism 425 responsive to input received from a user 480.

The processor 430 may be configured to apply the at least one filter mechanism 425 to the ECG data to at least substantially remove chest compression artifacts from the ECG data, wherein the chest compression artifacts correspond to the chest compressions being delivered to the patient 482 by the mechanical chest compression device 485, and wherein the at least one filter mechanism 425 substantially rejects content in the frequency f plus content in at least one more frequency that is a higher harmonic to the frequency f. In certain embodiments, application of the at least one filter mechanism 425 to the ECG data reduces an amplitude of the chest compression artifacts by at least 20 dB relative to the input signal.

The processor 430 may be further configured to cause the display 470 to visually present the filtered ECG data to the user 480. Alternatively or in addition thereto, the processor 430 may be configured to cause an optional printer 439 to print out the filtered ECG data. In certain embodiments, the processor 430 may cause the filtered ECG to be stored, e.g., by a memory 438, for later review or downloading to a post-event review tool.

In certain embodiments, the processor 430 is preconfigured to apply the at least one filter mechanism 425. In other embodiments, the processor 430 may be configured to apply the at least one filter mechanism 425 to the ECG data responsive to input received from the user 480.

In certain embodiments, the ECG data is received in real-time. In other embodiments, the ECG data is received in a post-event review. In these embodiments, the ECG data may have been recorded from defibrillation patches or an ECG monitor having multiple leads, e.g., three or more leads. The at least one filter mechanism 425 may be applied to the ECG data regardless of whether the device that recorded the signal even had the at least one filter mechanism 425. Indeed, the ECG data could be provided, e.g., sent via e-mail, to another user who causes the at least one filter mechanism 425 to be applied thereto. Post-event filtering may be used for establishing the time of re-fibrillation or examining the signal characteristics prior to fibrillation, for example.

For a patient experiencing VF, VF quality measures such as median VF frequency, Amplitude Spectral Area (AMSA), and the scaling exponent may be used for deciding when to apply chest compressions to the patient 482 and when to defibrillate the patient 482. By applying the at least one filter mechanism 425, these parameters may be accurately measured during CPR.

The processor 430 may be configured to determine a pattern of the chest compression artifacts corresponding to the chest compressions being delivered to the patient 482. The pattern may be based on starting and stopping of the chest compressions being delivered to the patient 482, for example. The processor 430 may be configured to determine whether a chest compression artifact pattern matches an existing chest compression signature. In certain embodiments, the processor 430 may be further configured to merge information corresponding to the pattern with information corresponding to the predetermined pattern responsive to a determination that the pattern matches the existing chest compression signature. In other embodiments, the processor 430 may be configured to generate a new chest compression signature responsive to a determination that the pattern does not match the existing chest compression signature.

In certain embodiments, the processor 430 is configured to suppress application of the at least one filter mechanism 425 to the ECG data responsive to a determination that the mechanical chest compression device 485 is no longer delivering chest compressions to the patient 482. The processor 430 may be further configured to resume application of the at least one filter mechanism 425 to the ECG data responsive to a determination that the mechanical chest compression device 485 has resumed delivery of chest compressions to the patient 482. The presence and/or absence of chest compressions may be detected using a measurement of the impedance signal. For example, the RMS value of a one-second window of the impedance signal is generally a reliable indicator of chest compressions.

In certain embodiments, the processor 430 is configured to generate a report, e.g., CPR statistics, corresponding to the chest compressions that were delivered to the patient 482. Alternatively or in addition thereto, the processor 430 may be configured to generate a report corresponding to the mechanical chest compression device 485 that was used to deliver the chest compressions to the patient 482.

In certain embodiments, the processor 430 is further configured to monitor an impedance signal corresponding to the patient. An impedance waveform could be filtered to remove compression artifacts, for example, to allow for detection of ventilation artifacts or the presence of cardiac output. The processor 430 may be further configured to detect return of spontaneous circulation (ROSC) by applying a signal-averaging filter to the impedance signal, e.g., combining a comb filter with the signal-averaging filter.

In certain embodiments, the processor 430 is further configured to analyze the filtered ECG data. In these embodiments, the processor 430 may be further configured to determine a shock/no shock decision based on the analysis of the filtered ECG data.

In certain embodiments, the chest compressions are manually delivered to the patient 482 by the rescuer 480. In these embodiments, the rescuer 480 may use a metronome while delivering the chest compressions to the patient 482 in order to deliver compressions at a very precise rate, for example. The processor 430 may be configured to select the at least one filter mechanism 425 based at least in part on a chest compression rate corresponding to the chest compressions being delivered to the patient 482. These embodiments may further include informing the rescuer 480 whether the CPR is currently effective, i.e., the chest compressions are being administered at the correct rate. The rescuer 480 may thus judge whether to trust the filtered display 470.

In certain embodiments, the device 400 further includes an energy storage module within the housing 401 for storing an electrical charge and a defibrillation port for guiding via electrodes the stored electrical charge to the patient 482.

Figure 5:
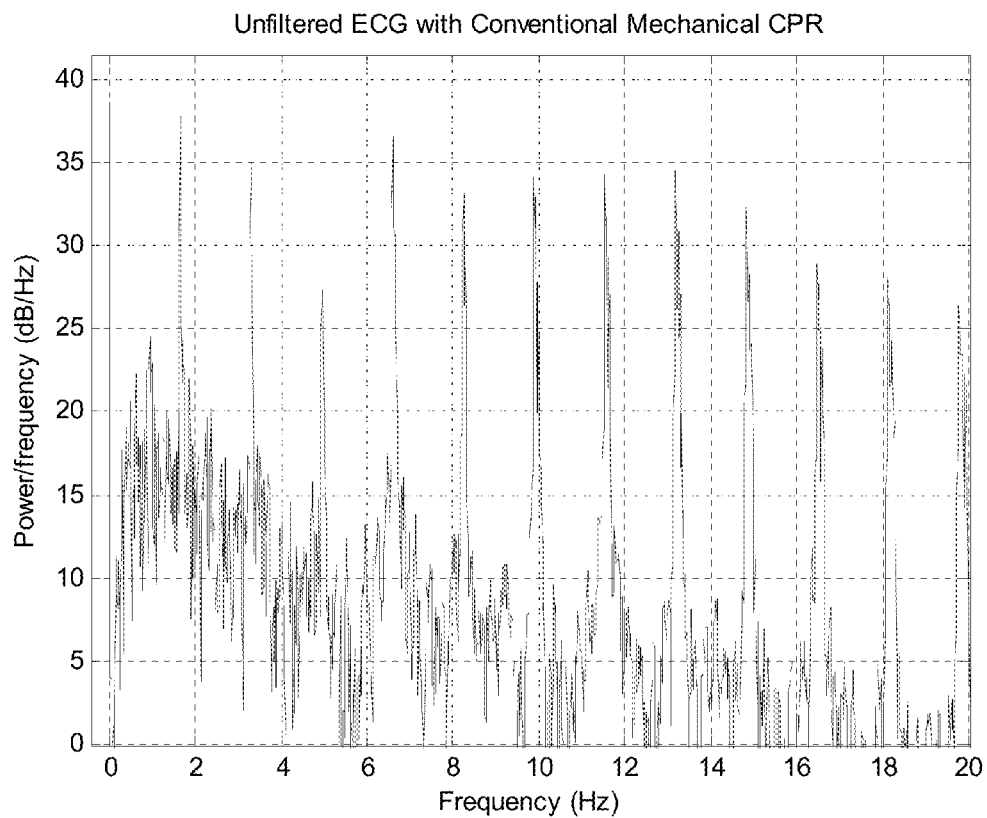
FIG. 5 is a graphical illustration of a fast Fourier transform of an ECG signal of an asystolic patient receiving chest compressions from a conventional mechanical chest compression device.

FIG. 5 is a graphical illustration of a fast Fourier transform of an ECG signal of an asystolic patient, such as patient 482 of FIG. 4, receiving chest compressions from a conventional mechanical chest compression device. As can be seen from the illustrated example, the ECG signal from an asystolic patient generally contains only artifacts because the patient has no active cardiac signal. Multiple spectral peaks are evident, with the fundamental frequency of the chest compressions appearing at 1.6 Hz and other peaks representing harmonic frequencies. The width of these spectral peaks varies from approximately 0.15 Hz at the fundamental frequency up to approximately 0.5 Hz for the $6^{th}$ harmonic (10 Hz). It would be difficult to remove the CPR artifact from the illustrated signal due to the requirement for a relatively wide filter, which would necessarily remove much of the cardiac signal, thus causing distortion that would adversely impact the signal.

Signals corresponding to conventional mechanical CPR devices generally have only broad spectral peaks, and the locations of such peaks are typically not precisely controlled. The fundamental frequency may vary from one device to another, or from one application to another. For example, the fundamental frequency may vary from 1.4 Hz to 1.7 Hz. Such variation generally prevents application of a non-adaptive filter, e.g., a comb filter, with a narrow stop band.

Conventional CPR artifact filters have been unsuccessful at removing CPR artifacts, in part, because they typically focus on removing the fundamental frequency while paying little, if any, attention to the harmonic frequencies. In the example illustrated by FIG. 5, the 12$^{th}$ harmonic is only about 11 dB down from the fundamental frequency. In one example, to produce a clean ECG signal, CPR artifacts usually need to be attenuated by at least 20 dB, and possibly as much as 40 dB. In order to clean up the signal, frequencies up to at least the 12$^{th}$ harmonic must typically be removed.

Figure 6:
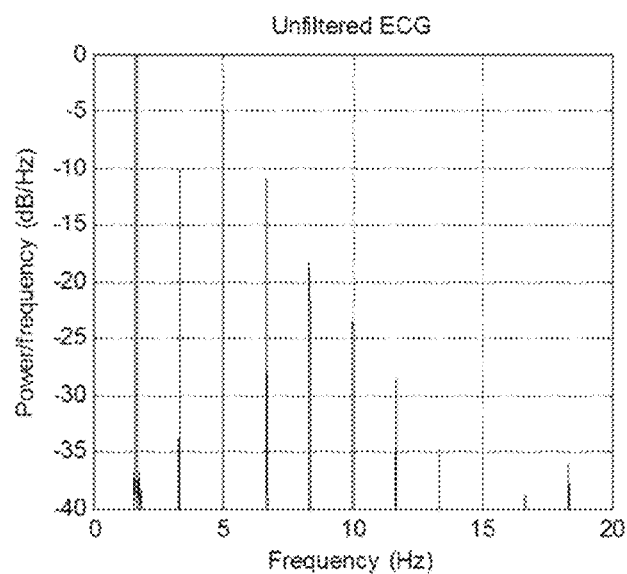
FIG. 6 is a graphical illustration of a fast Fourier transform of an ECG signal from an asystolic patient receiving chest compressions from a mechanical chest compression device having precise frequency control according to embodiments.

FIG. 6 is one embodiment of a graphical illustration of a fast Fourier transform of an ECG signal from an asystolic patient, such as the patient 482 of FIG. 4, receiving chest compressions from a mechanical chest compression device having precise frequency control according to embodiments. The spectral peaks of the artifacts generated by this device are typically very narrow, e.g., less than 0.1 Hz wide. This narrow spectral content enables the cardiac ECG signal to be separated from chest compression artifact. As with the signal of FIG. 5, multiple frequency harmonics are present in the signal of FIG. 6, in which the 5$^{th}$ harmonic is less than 20 dB down and the 11$^{th}$ harmonic is less than 40 dB down. In order to clean up the signal, harmonics up to at least the 5$^{th}$ harmonic, and possibly as high as the 11$^{th}$ harmonic, should be removed.

Figure 7:
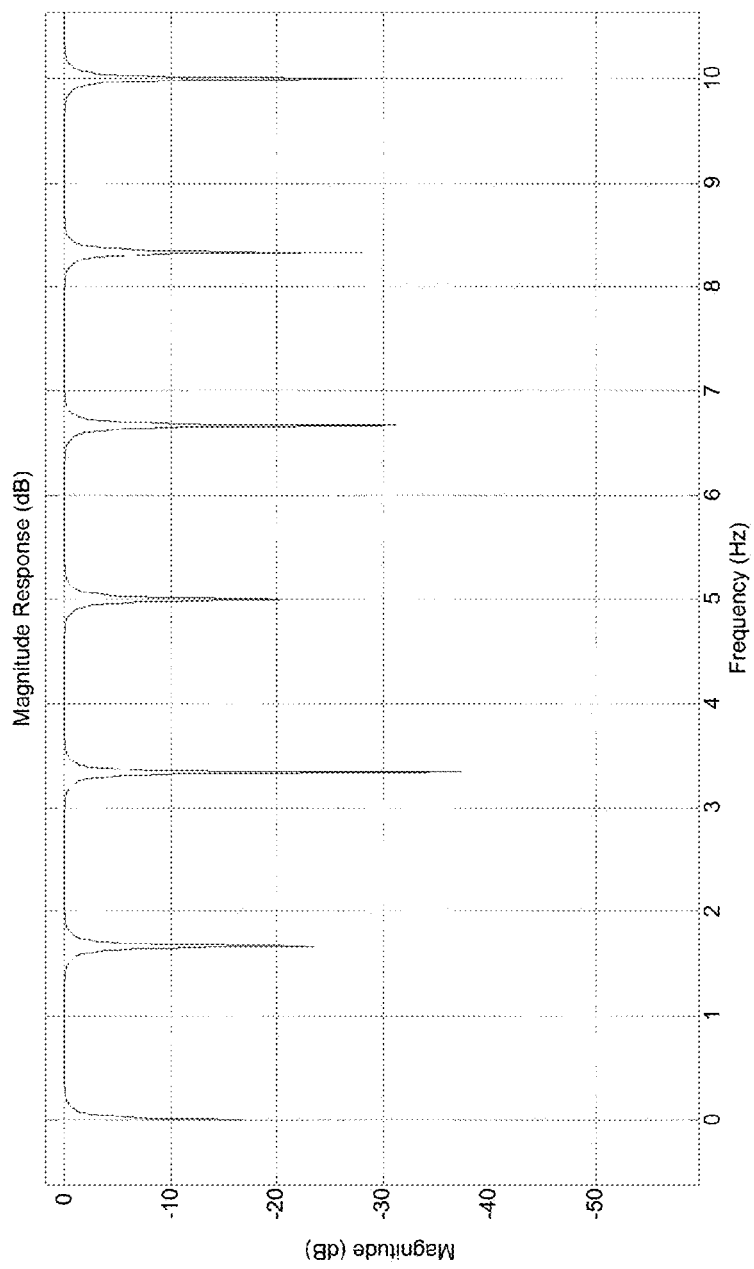
FIG. 7 is a graphical illustration of the frequency response of a comb filter suitable for removing chest compression artifacts from an ECG signal according to embodiments.

FIG. 7 is a graphical illustration of one embodiment of the frequency response of a comb filter, such as a high-Q comb filter, e.g., Q=16, suitable for removing chest compression artifacts from an ECG signal according to embodiments. A comb filter intrinsically removes the fundamental frequency and all of the harmonics. If the Q is set relatively high, e.g. 16, the filter will surgically remove the artifact frequencies and leave the other frequencies relatively untouched.

In general, high-Q filters are more frequency-selective than low-Q filters. For example, a comb filter having Q=16 will generally have a 3 dB notch width of about 0.1 Hz, whereas a comb filter having Q=4 will typically have a 3 dB notch width of about 0.5 Hz. A filter having Q=2 has approximately a 3 dB notch width of about 1 Hz and usually removes almost as much of the signal as it retains. A lower-Q filter will generally remove more artifacts from a signal than a high-Q filter but will also remove more of the signal itself. In addition, a low-Q filter tends to produce more ringing, which often provides additional distortion.

In one embodiment, to effectively remove CPR artifacts resulting from application of a conventional chest compression device, a very low-Q filter is preferable. Assuming that at least 20 dB of attenuation is needed, even a filter having Q=2 may not be effective in removing the artifact from the signal due to the spectral peaks of the artifact being too tall and too broad.

Because the spectral content of a mechanical CPR device according to embodiments is generally narrow, a high-Q filter is used to remove the compression artifact and retain the cardiac ECG signal with little distortion. Because a mechanical CPR device according to embodiments generally produces compressions at a precisely known frequency, the artifact may be filtered using a non-adaptive filter. Combining these two aspects (narrow frequency content and precise frequency control) according to embodiments thus enabled a high-Q comb filter to be used as an effective filter for removing CPR artifacts from the input signal.

By way of an example, the following is a Z transform of a suitable comb filter:

$$H(z) = \frac{a(z^{-1} - z^{-n})}{1 - bz^{-n}}$$

where "a" is a gain constant, "b" sets the filter Q, and "n" is an integer that sets the notch frequencies. The Q of this filter may be set by a single coefficient, the gain constant "b." For example, b=0.82 for a Q of 16. The value of "n" and the sample frequency may be set to locations of the comb notch frequencies. In situations where n=75 and the sample rate is 125 Hz, for example, the notch frequencies would be 1⅔ Hz, 3⅓ Hz, 5.0 Hz, etc.

In a further embodiment, a comb filter generally introduces very little signal delay. The signal is typically delayed only one sample, which is 8 milliseconds at 125 Hz, for example. From a user's standpoint, this delay is imperceptible. This is in contrast to certain filter structures, such as finite impulse response (FIR) filters, that can delay the signal by a second or more. Such delay could lead to a misalignment between the filtered ECG and other signals, such as the unfiltered ECG or an invasive blood pressure waveform, confusing to the user. Alternatively or in addition thereto, a collection of narrow notch filters, e.g., one filter for the fundamental frequency and one for every harmonic that needs to be removed, may be used. This small delay may make a comb filter particularly suitable for an ECG display, in which signal delays or misalignment with other monitoring parameters may be objectionable.

Figure 8:
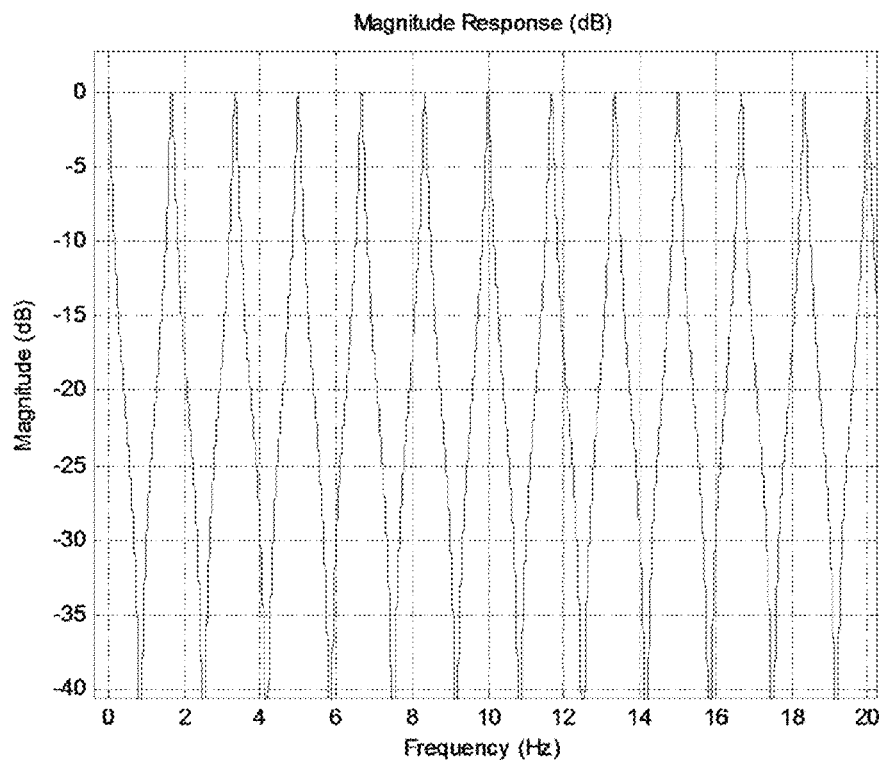
FIG. 8 is a graphical illustration of the frequency response of an inverse comb filter suitable for removing chest compression artifacts from an ECG signal according to embodiments.

FIG. 8 is a graphical illustration of the frequency response of an inverse comb filter suitable for detecting chest compression artifacts from an ECG signal according to embodiments. An inverse comb filter is generally similar to a comb filter except that it passes the comb frequencies instead of rejecting them. Such an inverse comb filter may be particularly suitable for detection of mechanical compressions delivered at certain rates, e.g., 100 compressions/minute.

Figure 9:
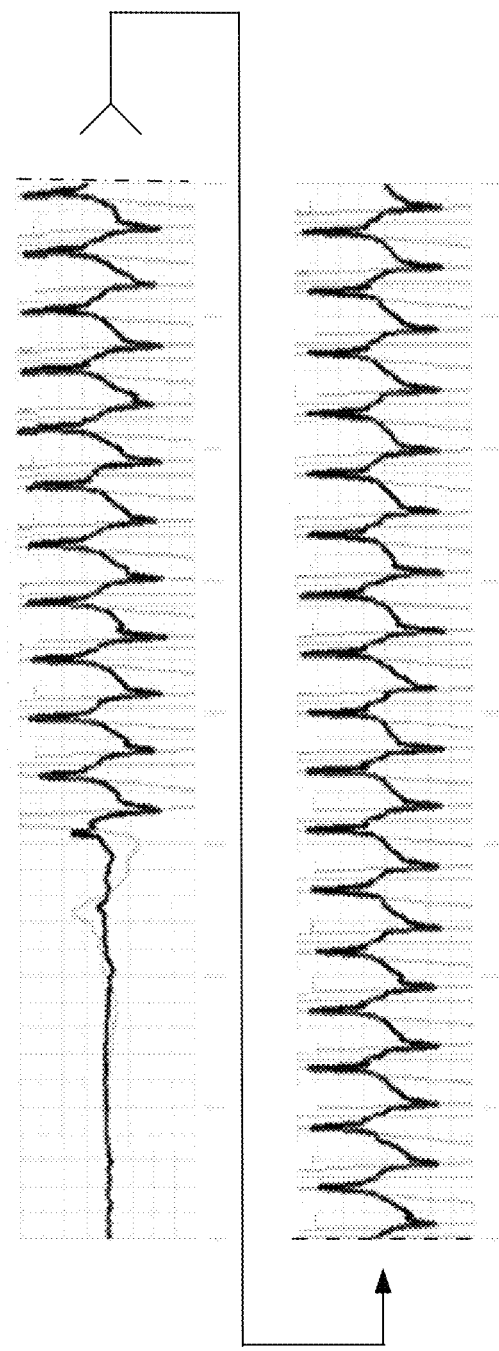
FIG. 9 is a time diagram of patient ECG data in the form of signals.

FIG. 9 is a time diagram of patient ECG data in the form of signals. The ECG data in this example is presently exhibiting an impulsive waveform having signal spikes or peaks that include both positive peaks and negative peaks. For example, the ECG data of FIG. 9 may generally correspond to a patient, such as the patient 482 of FIG. 4, that is neither experiencing a cardiac event nor receiving chest compressions, e.g., from a chest compression device such as the mechanical chest compression device 485 of FIG. 4.

Figure 10:
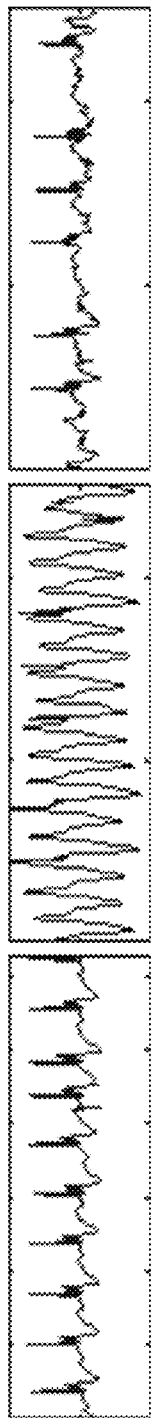
FIG. 10A is a time diagram of an ECG signal having QRS complexes and no chest compression artifacts.
FIG. 10B is a time diagram of an ECG signal having QRS complexes and chest compression artifacts with no filtering.
FIG. 10C is a time diagram of an ECG signal having QRS complexes and chest compression artifacts with a filter mechanism applied thereto.

FIG. 10A is a time diagram of an ECG signal having QRS complexes and no chest compression artifacts. The QRS complexes generally include both positive peaks and negative peaks. As with the ECG data of FIG. 9, the ECG signal of FIG. 10A may generally correspond to a patient, such as the patient 482 of FIG. 4, that is neither experiencing a cardiac event nor receiving chest compressions, e.g., from a chest compression device such as the mechanical chest compression device 485 of FIG. 4.

FIG. 10B is a time diagram of an ECG signal having QRS complexes and chest compression artifacts with no filtering. For example, the ECG signal of FIG. 10B may generally correspond to a patient, such as the patient 482 of FIG. 4, that is not necessarily experiencing a cardiac event but is presently receiving chest compressions, e.g., from a chest compression device such as the mechanical chest compression device 485 of FIG. 4. As can be readily ascertained by even a causal viewer, the QRS complexes in the ECG signal are at least partially, if not fully, obscured by the chest compression artifacts.

FIG. 10C is a time diagram of an ECG signal having QRS complexes and chest compression artifacts with a filter mechanism, such as the filter mechanism 425 of FIG. 4, applied thereto. The effect of such application is readily apparent. Indeed, the time diagram of FIG. 10C is significantly closer in appearance to the time diagram of FIG. 10A than to the time diagram of FIG. 10B. One can even readily discern P-waves and inverted T-waves in the time diagram. Further, a QRS detector could use the filtered waveform to provide an accurate intrinsic heart rate indication during delivery of chest compressions to the patient.

Figure 11:
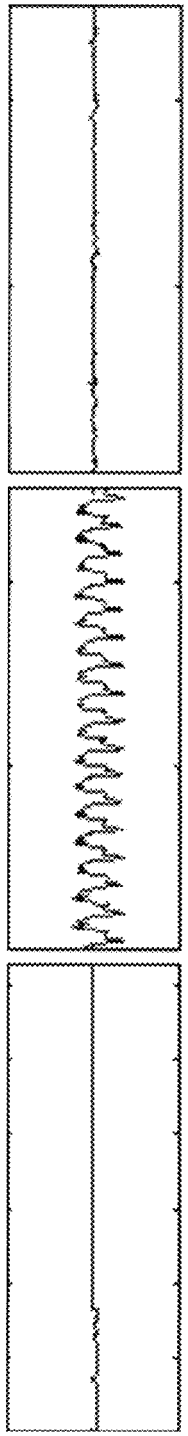
FIG. 11A is a time diagram of an ECG signal having no QRS complexes and no chest compression artifacts.
FIG. 11B is a time diagram of an ECG signal having no QRS complexes and chest compression artifacts with no filtering.
FIG. 11C is a time diagram of an ECG signal having no QRS complexes and chest compression artifacts with a filter mechanism applied thereto.

FIG. 11A is a time diagram of an ECG signal having no QRS complexes and no chest compression artifacts. For example, the ECG signal of FIG. 11A may generally correspond to a patient, such as the patient 482 of FIG. 4, that is currently experiencing asystole but to whom chest compressions have not yet been applied, e.g., from a chest compression device such as the mechanical chest compression device 485 of FIG. 4.

FIG. 11B is a time diagram of an ECG signal having no QRS complexes and chest compression artifacts with no filtering. For example, the ECG signal of FIG. 11B may generally correspond to a patient, such as the patient 482 of FIG. 4, that is currently experiencing asystole and to whom chest compressions are being concurrently applied, e.g., from a chest compression device such as the mechanical chest compression device 485 of FIG. 4.

FIG. 11C is a time diagram of an ECG signal having no QRS complexes and chest compression artifacts with a filter mechanism, such as the filter mechanism 425 of FIG. 4, applied thereto. As with the time diagram of FIG. 10C, the effect of such application is readily apparent here. Indeed, the time diagram of FIG. 10C is significantly closer in appearance to the time diagram of FIG. 10A than to the time diagram of FIG. 10B.

Figure 12:
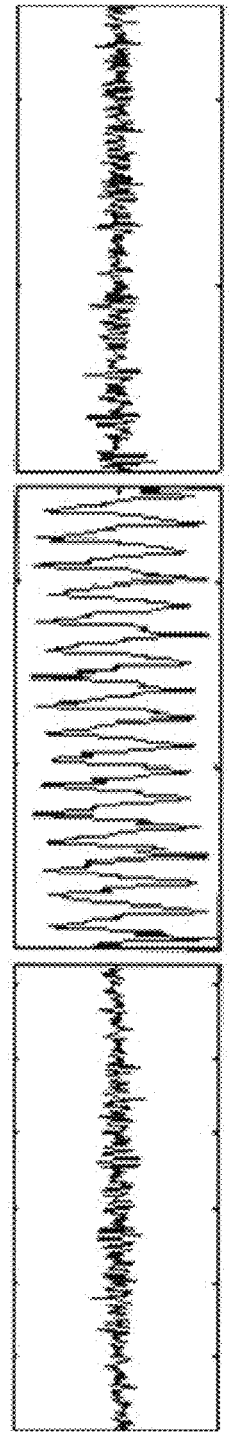
FIG. 12A is a time diagram of a VF signal having no chest compression artifacts.
FIG. 12B is a time diagram of a VF signal having chest compression artifacts with no filtering.
FIG. 12C is a time diagram of a VF signal having chest compression artifacts with a filter mechanism applied thereto.

FIG. 12A is a time diagram of a VF signal having no chest compression artifacts. For example, the VF signal may generally correspond to a patient, such as the patient 482 of FIG. 4, that is currently experiencing VF but to whom chest compressions have not yet been applied, e.g., from a chest compression device such as the mechanical chest compression device 485 of FIG. 4.

FIG. 12B is a time diagram of a VF signal having chest compression artifacts with no filtering. For example, the VF signal may generally correspond to a patient, such as the patient 482 of FIG. 4, that is currently experiencing VF and to whom chest compressions are being concurrently applied, e.g., from a chest compression device such as the mechanical chest compression device 485 of FIG. 4.

FIG. 12C is a time diagram of a VF signal having chest compression artifacts with a filter mechanism, such as the filter mechanism 425 of FIG. 4, applied thereto. As with the time diagrams of FIGS. 10C and 11C, the effect of such application is readily apparent here. Indeed, the signal presented by the time diagram of FIG. 10C is significantly closer in appearance to the signal presented by the time diagram of FIG. 10A than to the signal presented by the time diagram of FIG. 10B.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines, computers may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical device, physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features or algorithm, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Filter Mechanism Method for Removing EGG Artifact from CPR

Figure 13:
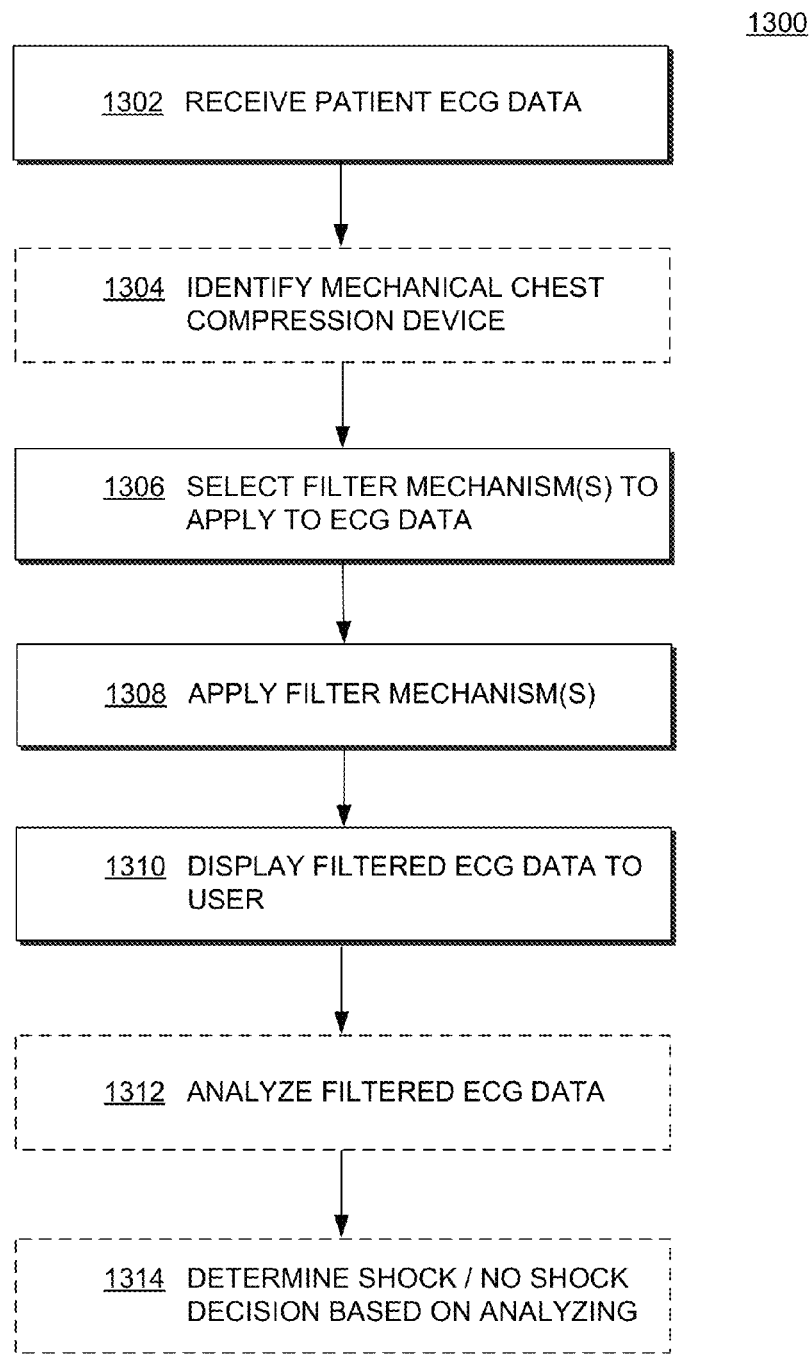
FIG. 13 is a flowchart for illustrating methods according to embodiments.

FIG. 13 is a flowchart 1300 for illustrating methods according to embodiments. The methods of flowchart 1300 may be practiced by systems, devices, and software according to embodiments. For example, the methods illustrated by flowchart 1300 can be performed by the external medical device 400 illustrated in FIG. 4.

According to an operation at 1302, a signal containing ECG data for a patient receiving chest compressions from a mechanical chest compression device as the mechanical chest compression device 485 of FIG. 4 is received. The mechanical chest compression device has a chest compression frequency f. Certain embodiments may include detecting the chest compressions being delivered to the patient.

According to an optional operation at 1304, the mechanical chest compression device is identified. In certain embodiments, a processor, such as the processor 430 of FIG. 4, may perform the identifying. In other embodiments, the chest compression device may send identifying information to the processor.

According to a next operation at 1306, at least one filter mechanism is selected. The selecting may be based on a chest compression rate, a sample rate of the ECG data, an identification of the mechanical chest compression device being used to deliver the chest compressions to the patient, or a combination thereof.

The at least one filter mechanism may include a comb filter, an inverse comb filter, a matched filter, a plurality of notch filters, or any suitable combination thereof. In embodiments including a comb filter, the comb filter may be non-adaptive. In embodiments including a plurality of notch filters, each of the notch filters may be non-adaptive.

According to a next operation at 1308, the at least one filter mechanism selected at 1306 is applied to the received signal to at least substantially remove chest compression artifacts from the ECG data, wherein the chest compression artifacts correspond to the chest compressions being delivered to the patient by the mechanical chest compression device.

According to a next operation at 1310, the filtered ECG data may be visually presented to a user, e.g., via a display such as the display 470 illustrated in FIG. 4.

According to an optional operation at 1312, the filtered ECG data is analyzed. Any of a wide variety of suitable techniques may be used in the analyzing.

According to an optional operation at 1314, a shock/no shock decision is determined based on the analyzing. For example, a shock decision may be determined based on a result of the analyzing that indicates no QRS complexes are present in the filtered ECG data. Conversely, a no shock decision may be determined based on a result of the analyzing that indicates QRS complexes are present in the filtered ECG data.

In certain embodiments, methods may further include storing an electrical charge and guiding via electrodes the stored electrical charge to the patient.

Figure 14:
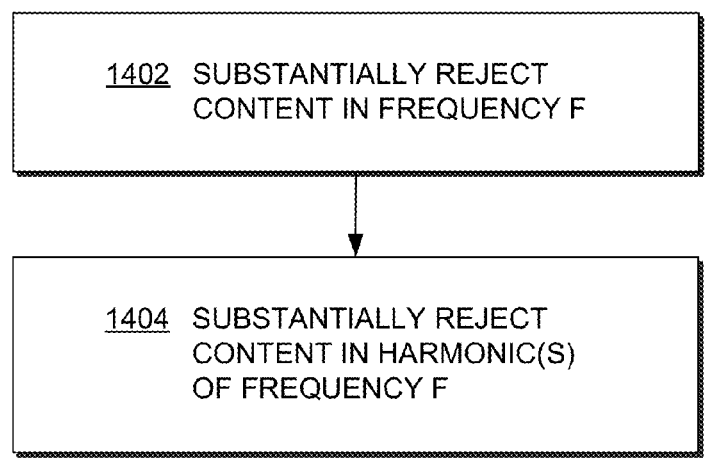
FIG. 14 is a flowchart for illustrating other methods according to embodiments.

FIG. 14 is a flowchart 1400 for illustrating other methods according to embodiments. In particular, the flowchart 1400 corresponds to the operation 1308 of the methods illustrated by the flowchart 1300 of FIG. 13.

According to an operation at 1402, content in the frequency f is substantially rejected by the at least one filter mechanism. Consequently, an amplitude of chest compression artifacts at the frequency f may be reduced, e.g., by at least 20 dB relative to the input signal.

According to a next operation at 1404, content in at least one more frequency that is a higher harmonic to the frequency f is substantially rejected by the at least one filter mechanism. As with the content in the frequency f, an amplitude of chest compression artifacts, at each higher harmonic to the frequency f may be reduced, e.g., by at least 20 dB relative to the input signal.

Figure 15:
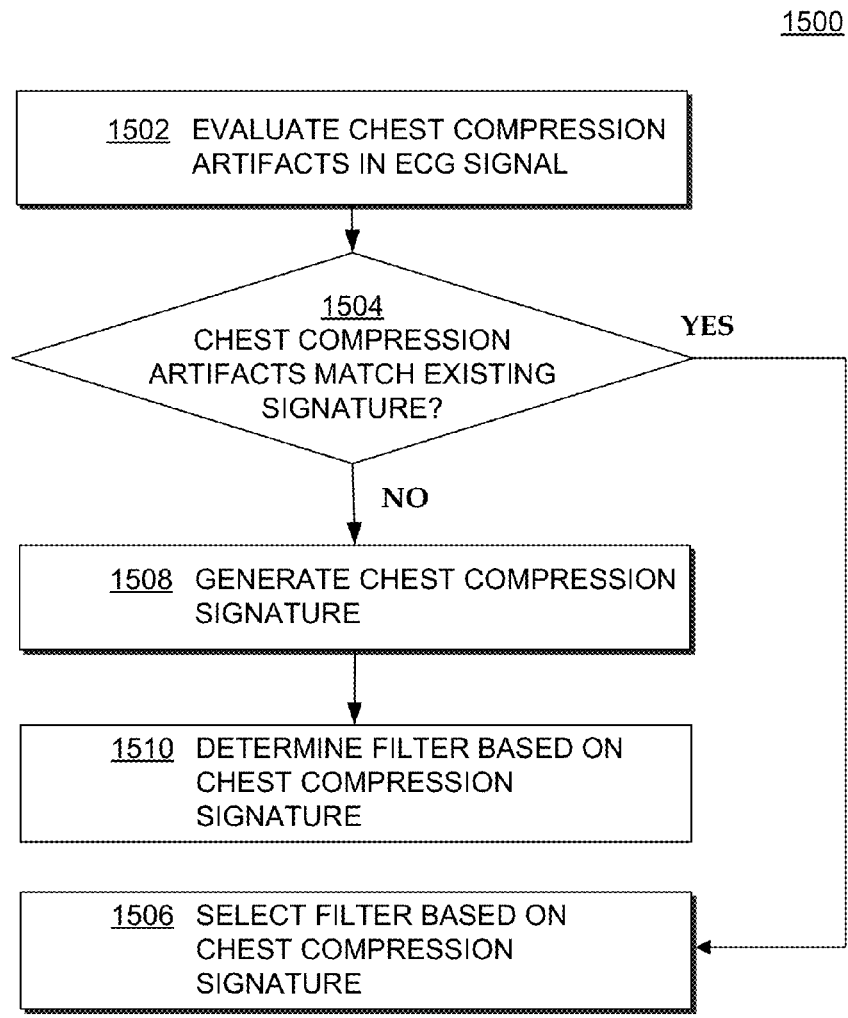
FIG. 15 is a flowchart for illustrating other methods according to embodiments.

FIG. 15 is a flowchart for illustrating other methods according to embodiments.

According to an operation at 1502, chest compression artifacts in a signal containing ECG data for a patient receiving chest compressions from a mechanical chest compression device are evaluated. For example, a pattern of chest compression artifacts corresponding to the chest compressions being delivered to the patient may be determined. The pattern may be based on starting and stopping of the chest compressions being delivered to the patient, for example.

According to an operation at 1504, a determination is made as to whether the pattern matches an existing chest compression signature. Responsive to a determination that the pattern matches an existing chest compression signature, the method proceeds to an operation at 1506; otherwise, the method proceeds to an operation at 1508.

According to the operation at 1506, a filter mechanism, such as the filter mechanism 425 of FIG. 4, is selected based on the existing chest compression signature. In certain embodiments, information corresponding to the pattern may be merged with information corresponding to the predetermined pattern.

According to the operation at 1508, a new chest compression signature is generated based on the pattern.

According to a next operation at 1510, a filter mechanism, such as the filter mechanism 425 of FIG. 4, is selected based on the chest compression signature generated at 1508.

Certain embodiments may include determining whether the mechanical chest compression device is still delivering chest compressions to the patient. These embodiments may further include suppressing the applying responsive to a determination that the mechanical chest compression device is no longer delivering chest compressions to the patient.

Certain embodiments may include monitoring an impedance signal corresponding to the patient. These embodiments may further include applying a signal-averaging filter to the impedance signal to detect a return of spontaneous circulation (ROSC).

ECG Frequency Analysis During CPR

Additionally, in some cases, patients with more than five minutes of VF benefit from one to two minutes of CPR prior to defibrillation. VF frequency decreases with VF duration. CPR increases the VF frequency. The VF frequency may act as a surrogate for the condition of the cardiomyocytes, which deteriorate when deprived of circulation (e.g. during unsupported VF) and "perk up" when oxygenated (during CPR). Patient outcomes are better if a shock is delivered with the heart cells are more "alert." Shocks delivered to poor quality VF are likely to result in asystole, PEA, or more VF. Although some VF patients clearly benefit from CPR prior to defibrillation, the optimal amount of CPR has, to-date, proven difficult to assess.

The present subject matter discloses a system and method for administering an optimal amount of CPR to a patient such as the patient 482 of FIG. 4, by allowing the amount of CPR to be adjusted to compensate for variable downtimes and for variable CPR quality, especially in cases when a rescuer performing CPR is a person.

Figure 16:
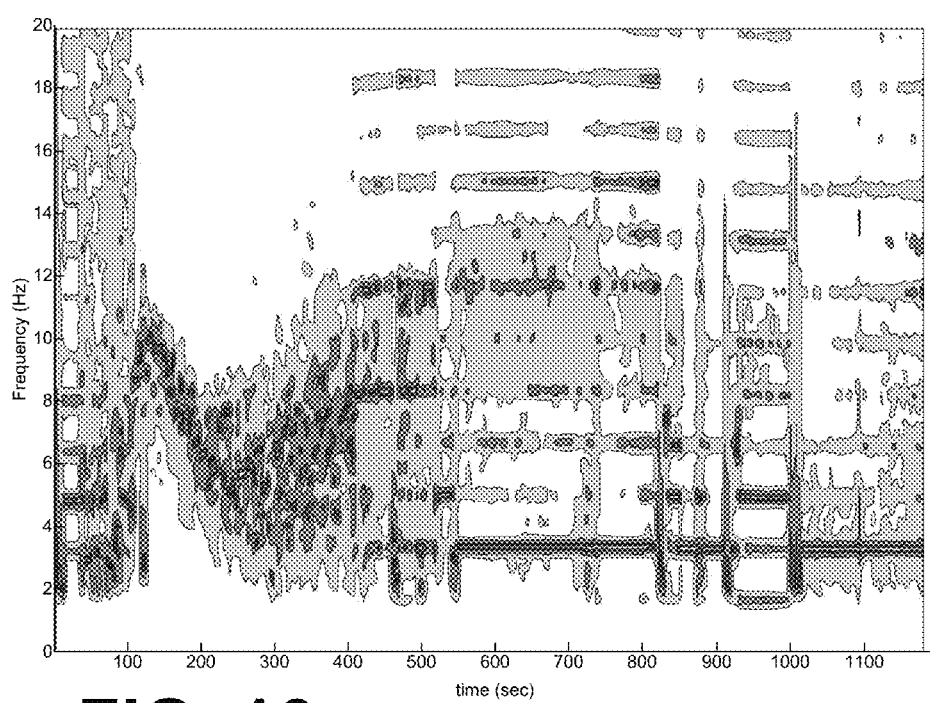
FIG. 16 is a diagram of frequency spectrum monitored over time.

FIG. 16 demonstrates an embodiment representation of ECG frequency spectrum monitored over time, where frequency is measured in Hertz (Hz) and time in seconds (sec). In this example, the optimal amount of CPR is determined prior to defibrillation and coordination of CPR and defibrillation based on the ECG analysis. VF at about 120 seconds is continuing unsupported until about 410 seconds. At that point, CPR is started. CPR continues until about 830 seconds, at which point a series of defibrillation shocks are provided. FIG. 16 demonstrates that the peak VF frequency started at about 10 Hz (at about 120 seconds) and then, began to drop and spread out. After CPR created artifact but the VF frequency can be seen to increase for 200-300 seconds, after which it began to gradually fall again.

The peak VF frequency indicates the time when the heart is able to support circulation. The improvement during CPR occurs as oxygenated blood is circulated to the heart. The deterioration that occurs near the end of the CPR period occurs because the amount of circulation provided during CPR is inadequate to support the metabolic needs of the heart.

FIG. 16 further illustrates frequency spectrum spreading out over time during unsupported VF. At 120 seconds the distribution of frequencies is only a few Hertz, but at 400 seconds it is approximately 8-10 Hz. After CPR starts, the VF frequency increases and the distribution of frequencies is also reduced. By 750 seconds the frequency distribution is down to 2-3 Hz. Both VF frequency and VF frequency range provide an indication of VF quality. Determination in how much CPR to perform before defibrillating is administered is based on the VF quality. As demonstrated by FIG. 16, the optimal time to shock is either the point when the VF frequency is at a maximum or when the spread of frequencies is at a minimum. In a further embodiment, the above-described measures are combined with each other or with other measures such as VF amplitude to provide a stronger indication VF quality. For example, calculating the area under the frequency curve provides a single measure, which includes both frequency and distribution.

FIG. 16 also illustrates an approach of effectively compensating for differing down times and VF quality. Poor CPR quality results in little or no increase in VF quality, or retards the speed at which an optimal value is reached. A shorter (or longer) VF duration may cause the heart to respond more quickly (or more slowly).

In one embodiment, VF frequency content is demonstrated by applying the Welch method of frequency estimation using 2048 data points and a 1024 sample window. The signal is taken from the defibrillator paddles channel, which is sampled at 125 hz. The filtered signal is high-passed with a 10 pole 2 Hz Butterworth high-pass filter. A separate spectral analysis is performed each second. The amplitude of each spectrum is normalized to the peak value in that time slice. FIG. 16 is a contour plot, but other methods of illustrating the three-dimensional data may be used as would be apparent to one skilled in the art. In this example, visually, the CPR artifact from the VF signal is separated because the artifact happens in narrow multiples of the CPR rate, which was 1.6 Hz, by way of an example. CPR artifact can be removed from this spectrum simply by setting all the multiples of a certain value such as 1.6 Hz to zero. This method removes some of the VF frequency content, but leaves enough of the VF signal to allow adequate frequency estimation. It should be appreciated that this disclosure offers a long-sought solution in cardiac resuscitation.

ECG in CPR Utilizing Shock History and Compensating for Expected Noise

While a correct shock decision can be properly made during CPR, there is a subset of patient signals that contains excessive noise, which may prevent analysis. This subset can be automatically identified and excluded from analysis during CPR but this approach also carries the risk of excluding cases in which the automatic analysis would have been successful. Amplitude of CPR artifact is much greater in patients who have not received a defibrillation shock than in those patients who have been shocked. The task of analyzing during CPR is easier after a shock has been delivered than before.

Therefore, the present disclosure adjusts analysis algorithm parameters based on whether a shock has been delivered or not. Prior to delivering a shock, the algorithm may be biased toward pausing CPR to allow a "clean", meaning uninfluenced by CPR artifact, analysis and evaluation if there is any doubt about analysis accuracy. After delivering a shock, the algorithm is biased in favor of minimizing pauses and accepting the analysis results in recognition of the fact that the artifact is smaller and the analysis quality improves after shocking.

Figure 17:
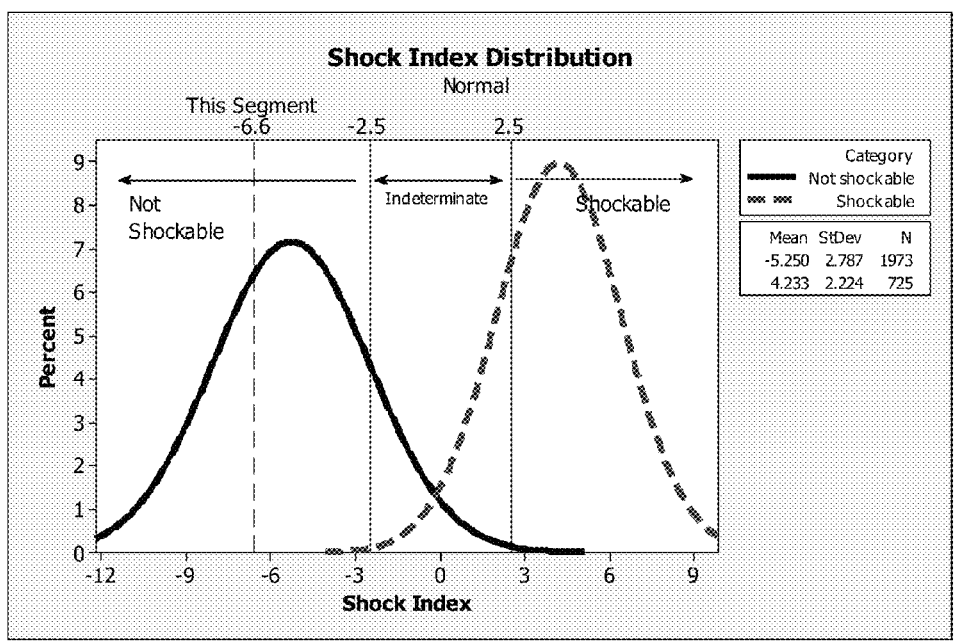
FIG. 17 is a shock index distribution diagram.

FIG. 17 illustrates one embodiment where parameters of an ECG (or other waveform) are adjusted and analysis module takes into account whether a patient has been previously shocked with a defibrillator. This method implements a shock analysis algorithm configured to analyze the patient's rhythm during CPR chest compressions. The nature of the signals, and consequently the performance of the method, changes subsequent to shock delivery. The shock history is therefore used to adjust parameters and to optimize performance based on whether a shock has been delivered, as illustrated in FIG. 17.

For further illustrative purposes, one approach is a rhythm analysis algorithm that measures parameters X and Y to make a shock decision. Examples of parameters that might be used are the ECG amplitude, frequency, median frequency, rate of zero crossings, impedance, etc. Other parameters are possible as would be obvious to one skilled in the art. To recommend shock, the value of X is to exceed threshold 1 and Y is to exceed threshold 2. However, threshold 1 and threshold 2 may change and be different depending on whether the defibrillator had delivered a shock to that patient or not. In the present disclosure, the revised thresholds compensate for the fact that the pre-shock ECG is expected to contain more noise than the post-shock ECG. Alternatively, the algorithm may implement the following formula to make a shock/no shock decision:

$$Index = A*X + B*Y + C$$

Here, X and Y are measured waveform parameters, and A, B, and C are constants. A shock is recommended if Index exceeds a threshold, and no-shock is recommended, if Index is less than the threshold. In present subject matter, on the other hand, the threshold value for Index changes after a shock has been delivered, or alternatively, the values of A, B, and C change.

In a further embodiment, certain parameters, which are useful post-shock are not be reliable pre-shock if the noise sensitivity of different measured parameters varies. Some parameters are so sensitive to noise that they are not useful for patients that have not been previously shocked. To compensate, this method will invoke different parameters for patients who have been previously shocked than for those that Shave not been previously shocked.

In a further embodiment, the Index formula, as described above, is tailored to allow for three recommendations: shock, no-shock, and indeterminate. Index values above an upper threshold give a shock recommendation, values below a lower threshold give a no shock recommendation, and values between the upper and lower thresholds give an indeterminate result. The upper and lower thresholds, accordingly, are farther apart for patients that have not been shocked, but closer together for patients that have been shocked resulting in more indeterminate values for unshocked patients and fewer indeterminate results for patients who have been shocked. This approach compensates for the noisy unshocked ECG signals by using a larger indeterminate zone for unshocked patients. Patients who have been previously shocked may have a small or nonexistent indeterminate zone, resulting in few if any indeterminate recommendations. In one embodiment, the Shock Index is a numerical value calculated based on measured patient waveform parameters. The algorithm recommends a shock for patients with a high shock index value, no shock for patients with a low shock index value, and gives an indeterminate result for values in the middle (near zero).

FIG. 17 further illustrates an example of an overlap between the Shock Index values for the patients that are truly shockable versus those that are not shockable. This overlap could cause an incorrect shock recommendation. By way of an example, consider a system with a single shock/no shock threshold of zero. If all patients with a shock index value above zero are considered shockable, then about 1% of non-shockable patients receive an incorrect shock recommendation. Similarly, if all patients below zero are considered non-shockable, then about 1% of shockable patients would receive an incorrect no-shock recommendation. Therefore, to minimize the number of incorrect shock recommendations, the present disclosure offers a two-threshold approach. Only those patients above the upper threshold or below the lower threshold receive a definite shock recommendation; patients in the indeterminate zone receive neither a shock nor a no-shock recommendation. The thresholds for the indeterminate zone are set in such a way as to as to minimize the number of incorrect shock recommendations.

There is more overlap between the Shock Index values for shockable and non-shockable patients who have not been previously shocked than there is for patients who have been previously shocked. As there is more noise on the ECG signal of a patient who has not been previously shocked, an unshocked patient needs a wide indeterminate zone in order to avoid incorrect shock results. In comparison, a previously shocked patient might have a narrow or non-existent indeterminate zone. This realization is useful for analysis-during-CPR. Definite shock/no shock recommendation during CPR can then be made and pauses avoided. On the other hand, if for any reason, the analysis-during-CPR is unable to make a definite evaluation and recommendation, the recommendation will be to pause for a "clean" analysis rather than to proceed with an incorrect therapy. Again, more pauses in CPR are recommended for patients who have not been previously shocked. In such cases, patients have their ECG signal analyzed during a pause in compressions, and thus, avoid the noise associated with CPR on an unshocked patient.

A person skilled in the art will realize that there are many ways of adjusting an analysis, evaluation, and recommendation of the present system and method, depending on whether or not a patient had been previously shocked. It is possible that the algorithm used for a patient who has not been previously shocked might be adjusted and customized to a patient depending on the patient's needs and prior patient history including ECG, CPR, and shock therapy. There are many ways of adjusting and customizing the parameters, as would be appreciated by one skilled in the art.

In another embodiment, a 12-lead interpretive algorithm that makes interpretive statements utilizes different thresholds depending on the expected noise level. Alternatively, an algorithm measuring the VF quality uses a measure such as AMSA, the scaling exponent, the median frequency, or the rotational velocity is adjusted depending on whether a shock had been delivered or not.

The present subject matter is further configured to assess a patient condition or measure a patient parameter using signals other than an ECG signal. For example, the patient impedance waveform is used in determining the condition of a patient. Such an impedance waveform is measured with an AC signal such as 20 kHz and is demodulated into real and imaginary components. The impedance waveform is then represented as having a magnitude and a phase. A patient assessment module utilizes the patients ECG in conjunction with the impedance signal to evaluate and reach a conclusion. Because the ECG signal tends to be more noisy for a patient that has not been shocked, it may be beneficial to adjust the algorithm parameters depending on whether the patient has been previously shocked.

In a further embodiment, there is the noise on the impedance signal of an unshocked patient versus a shocked patient is not higher. In other words, there is no reason to adjust the processing of the impedance signal based on the shock history. An analysis module that utilizes both the ECG signal and the impedance signal and the ECG signal processing parameters are adjusted based on the shock history but not adjust the impedance parameters. Shock history is used as an indicator of the amount of expected noise on an ECG signal. Other ways of anticipating the amount of noise include a low-frequency (<1 kHz) impedance measurement used as an indicator of the amount of expected noise.

To-date, defibrillators measure the patient impedance at a high frequency (10 kHz-100 kHz). A high frequency carrier signal is advantageous because such signal helps to separate the high-frequency impedance carrier signal from the ECG signal, which has a relatively low bandwidth. Also, AC signals in the range of 30 kHz-60 kHz have been shown to be useful for predicting the high voltage defibrillation shock impedance. On the other hand, a low-frequency impedance measurement is used when anticipating the amount of noise that might be expected on an ECG signal. When measured at a low frequency, a high impedance patient is expected to have a noisier ECG signal than a low impedance patient. Thus, an impedance measurement can be used to adjust an ECG analysis algorithm in a manner similar to the patient's shock status.

In one embodiment, an impedance measurement is made when the electrodes are applied to the patient or when the electrodes are still in the pouch. Some electrode systems include a conductive bridge between the two pads while they are in the pouch. This bridge allows the defibrillator to detect the presence of the electrodes and to assess whether the electrode gel has dried out using the impedance measurement. The bridge can take the form of a small wire between the two pads that is easily removed before the pads are applied to the patient. This allows the impedance measurement to be made while the electrodes are still in the pouch. This impedance may correlate with the amount of noise on the ECG signal. Thus, for an analysis algorithm one may adjust parameters based on an impedance measurement made while the electrodes are still in the pouch.

Other ways of predicting the amount of noise to be expected on a patient's ECG signal can be engaged. For example, the electrode chemistry may contribute to the amount of noise on the ECG signal. If an electrode with a noisier chemistry is used, algorithm parameters can be adjusted accordingly. Alternatively, some algorithms may be incongruent for use with some electrodes. In such situation an analysis module engages an algorithm enabled for some electrodes but disabled for other electrodes.

In a further embodiment, the electrode design contributes to the amount of noise. For example, a conventional 2-wire defibrillation pad is relatively sensitive to noise and artifacts. On the other hand, the amount of noise pickup can be reduced if a reference electrode is added to one of the pads. A reference electrode can be useful for reducing the noise on the ECG signal. A shielded electrode will be less sensitive to some kinds of noise than a non-shielded electrode. Also, a therapy pad with a separate, small ECG sensing pad built in can be less sensitive to noise. An AED analysis module is capable of engaging algorithm capable of compensating for these electrode configurations to account for the amount of expected noise. If the electrode in use produces a lower noise signal than a conventional electrode, the selected engaged matched algorithm analyzes with higher accuracy, requires fewer pauses for a clean analysis, or analyzes more quickly and effectively.

In one embodiment, the defibrillator, or a medical device, determines the type of electrode connected to the defibrillator and/or the patient. The defibrillator is capable of detecting the electrode type based on an automatic electrode identification scheme, such as a memory chip embedded in the electrode. Alternatively, the defibrillator is configured for a specific electrode type prior to use. Once the defibrillator has determined the electrode type, the system and method then selects and engages algorithm parameters accordingly.

In some circumstances, automated CPR machines create electrical noise, which is picked up on the ECG signal. The noise from the CPR machine can interfere with or aid analysis. When a defibrillator is used with a particular automated CPR machine, the present system and method, adjusts analysis, evaluation, and recommendation base on algorithm to account for the expected noise. The defibrillator, for example, becomes aware of the presence of a particular automated CPR machine either by signal analysis (for example, analysis of the impedance signal), by operator selection, by direct communication between the two machines, or by other mechanisms.

In a further embodiment, the electrode pad placement also contributes to the amount of noise observed on an ECG signal. While an anterior-lateral (A-L) position is most common, an anterior-posterior (A-P) placement is sometimes used. The A-P placement can result in a noisier ECG signal because the rescuer's hands are placed directly on top of the anterior pad. As such, the analysis module engages algorithm based on pad placement. The defibrillator may determine that the pads are likely to be placed in A-P position based on the pad type. For example, an infant-child electrode is more likely to be used in the A-P position because there is a limited amount of room on the chest of an infant, so it is reasonable to expect an infant-child electrode to be noisier than an adult electrode. Alternatively, an operator makes an AED selection and instructs the defibrillator to use the algorithm tailored to A-P position.

AED Operation Dependent on Previous Analysis Results

To date, defibrillators prompt for CPR for a fixed amount of time each CPR period, which is typically two minutes. While this fixed time period may be programmable at the time the AED is originally set up, it generally does not vary from one CPR cycle to another. A defibrillator may prompt the user to stop CPR at the end of the CPR period so that a rhythm analysis may be performed. The rhythm analysis is then generally performed once every CPR period. Thus, a given patient may have many rhythm analyses performed during the course of their care. The algorithm used for each of these rhythm analyses generally does not change from one analysis to another. In general, to-date, algorithms may measure some signal characteristics and compare those measured characteristics to thresholds to make a shock/no-shock decision. Typically, the same characteristics are measured and the same thresholds applied each time the rhythm is analyzed.

In contrast to prior attempts in the field, which as described above generally exhibit the same behavior each CPR period regardless of the results of previous rhythm analysis results, in the present disclosure, a defibrillator behavior in a given CPR period is dependent on previous rhythm analysis results. One aspect of this embodiment varies the CPR period and the associated prompts as a function of previous rhythm analysis results. In this embodiment, if the first AED analysis yields a "no shock advised," the CPR period can be different than if the first analysis result is "shock advised." In one embodiment, after an initial "no shock advised," the CPR period is modified such that CPR is performed indefinitely. No further rhythm analyses is then performed on that patient. Alternatively, the CPR period is lengthened. For example, the CPR period is lengthened from two minutes to five minutes. Alternatively, the AED is set up to prompt for CPR until another event is detected. Such an event can be a user action, such as a button press, or can be a device-detected event, such as electrode disconnection.

On the other hand, if the first rhythm analysis result is "shock advised," the device operates with normal CPR periods (i.e. an analysis every 2 minutes). These CPR periods can continue as long as the patient is treated by the defibrillator or they could be altered when another event is detected. Such an event might be, by way of an example, a user action, such as a button press, or it could be a device-detected event, such as electrode disconnection.

In a further embodiment the defibrillator changes the duration of the CPR period during the course of patient treatment. For example, the AED may be set up for an initial CPR period before the first analysis. By way of an example, this CPR period is programmable with a duration between 15 seconds and 3 minutes. If the first rhythm analysis yields a "no-shock" result, then the CPR period could change to another longer value, possibly 5 minutes. If a subsequent rhythm analysis yields a "shock advised" result, the CPR period could then change to a shorter period, possibly 2 minutes. Such a defibrillator has three different CPR periods, one for initial CPR, one for application after a "no shock" analysis, and one for application after a "shock advised" analysis. One skilled in the art will realize that other CPR periods could be applied under other circumstances that the AED may encounter.

In still another embodiment, a defibrillator alters the analysis algorithm as a result of previous analysis results. For example, the AED may use one analysis algorithm for the initial analysis and a different algorithm for subsequent analyses. If the initial analysis yields a "no shock" advised decision, then the subsequent analyses are performed with a different algorithm than if the initial analysis were "shock advised." Such an AED's analysis module has three algorithms, an "Initial Analysis" algorithm, a "Previously Non-Shockable" algorithm, and a "Previously Shockable" algorithm. The appropriate analysis algorithm is chosen based on previous analysis results. The algorithm can be chosen based on the results of the first analysis done on a patient, on the analysis immediately prior to the given analysis, or on other analyses that the device has performed on the patient. In one scenario the defibrillator uses the "Previously Non-Shockable" algorithm until a shock or a shockable rhythm has been observed, and then the "Previously Shockable" algorithm is engaged from then on. Similarly, other analysis algorithms are defined for use under other scenarios and applied under various circumstances as would be appreciated by one skilled in the art.

In a further embodiment, a medical device or a defibrillator alters the analysis module's algorithm based on a patient analysis other than a shock/no-shock decision. For example, if a patient has an initially non-shockable rhythm that contains QRS complexes, the algorithm used for subsequent analyses can be different than for an initially asystolic patient. Both rhythms are non-shockable, but different algorithms can be used for subsequent analyses. Similarly, different algorithms can be invoked for patients with initial bradycardia, normal sinus rhythm, supra-ventricular tachycardia, or other non-shockable rhythms. Along the same lines, different algorithms can be employed for subsequent analyses for a patient with initial "course" ventricular fibrillation (VF) as opposed to "fine" VF. Course VF can be distinguished from fine VF based on the peak-peak signal amplitude, or can be based a frequency analysis of the VF signal, an amplitude-frequency analysis such as AMSA, or other VF analysis method. The analysis algorithm can also be chosen based on previous patient hemodynamic information. A subsequent analysis in a patient that had previously exhibited a pulse can be different from a patient who never had a pulse detected. The algorithm selection can be based on the patient analysis at the time the medical device, such as and AED, is initially applied, on a patient analysis immediately prior to a given analysis, or an analysis performed at another point in time. For these purposes, the patient analysis can be an ECG analysis, or it can be an analysis of another patient signal or combination of signals. An analysis module includes an algorithm for quantitative evaluation of patient data and leads to a decision about a patient condition.

In a yet further embodiment, the analysis module can select from a plurality of algorithms and can further provide for flexible switching between algorithms. In one example, an algorithm is selected from a plurality of different algorithms for an initial analysis and for subsequent analyses, a different algorithm is selected. Further, the analysis module comprises different algorithms capable of analyzing the same parameters, but could apply different coefficients or different thresholds to each parameter. Alternatively, different parameters could be analyzed or a different process could be used for the different algorithms. A system of checks and balances can also be applied where several algorithms process parameters to verify results.

One way to incorporate multiple factors into a shock decision is achieved through the use of a formula such as:

ShockIndex=A*VFScore+InitialShockable+
  B*SubsequentVF+C, where ShockIndex=An overall
  numerical rating of likelihood the patient needs a shock
VF Score=A numerical rating of how much like VF the
  current rhythm is InitialShockable=A variable that
  takes on three distinct values depending on whether the
  initial rhythm was shockable, non-shockable, or
  unknown. The values would be calculated by regression analysis.
SubsequentVF=0 if no VF has been observed after the
  initial analysis, 1 if subsequent VF has been observed.
A, B, and C=Numerical weighting factors calculated by
  regression analysis.

As an example, a case in which a patient starts off in a non-shockable rhythm and fibrillates after 7 minutes of treatment and the AED is configured to prompt for initial CPR is considered below. Here is the time course of the device operation:

| Time | Device Behavior |
| --- | --- |
| Power On: | Device prompts for CPR |
| 2 Minutes: | Initial rhythm analysis is performed. If SHOCK ADVISED, analysis continues every 2 minutes. If NO SHOCK ADVISED, analysis interval changes to 4 minutes. |
| 6 Minutes: | Rhythm analysis in "Initially Non-Shockable" mode. This mode is biased toward higher specificity because of the initial non-shockable rhythm. If SHOCK ADVISED, analysis interval would switch back to 2 minutes. If NO SHOCK ADVISED, analysis interval stays at 4 minutes. |
| 10 Minutes: | Rhythm analysis in Initially Non-Shockable mode with 2 previous no-shock results. This mode is biased toward even higher specificity. If SHOCK ADVISED, analysis interval switches back to 2 minutes (as below). |
| 12 Minutes: | Rhythm analysis in Initially Non-Shockable mode with subsequent VF. |

As would be appreciated by one skilled in the art, this approach can be applied to an AED configured to analyze during CPR. Both the rhythm analysis algorithm and the analysis intervals can be influenced by history as described above.

In a further embodiment, analysis-during-CPR algorithms include a "continuous mode" which analyzes continuously during CPR and interrupts the CPR period if VF is detected. A continuous mode is recommended for patients with a high likelihood refibrillating, and not recommended if a patient has a very low probability of going into VF. If the odds of VF are low, a continuous mode can increase the likelihood of incorrectly indicating "shock advised" while providing little chance of detecting and terminating VF sooner. In such cases, rhythm analysis may carry a risk of an incorrect result. Thus, over-analyzing a patient unlikely to be in VF may do more harm than good.

To mitigate this concern, activation of continuous mode is made contingent on the patient history. An AED treating a patient with an initially non-shockable rhythm performs a rhythm analysis during CPR at the regular intervals (e.g. 2 minutes). However, an AED treating a patient with an initially shockable rhythm can switch to continuous mode because refibrillation is likely and the patient will benefit from earlier VF termination.

One skilled in the art will realize that there are many ways of displaying an analog value. The examples shown here are graphical, but it is possible that numbers could be displayed as well, or combinations of numbers and graphics. The Shock Index value could be displayed, or the probability of cardiac rhythm, VF, could be displayed, or some other numerical indicator that relates to the waveform.

Real-Time Cardiac Rhythm Quality & Rhythm Assessment Meter

The "VF Quality" degrades over time if CPR is not provided. VF quality can be measured in one or more ways, however, to-date, measuring VF quality during CPR has posed a significant challenge. Several methods have been proposed for using VF quality to guide therapy. One method applies shock immediately if VF quality is good and provides two minutes of CPR if it is poor. Another approach is to provide CPR until VF quality reaches a predetermined level.

The present embodiment offers a real-time VF quality indication to a rescuer/user during CPR. The indication might be a comparative scale of some type, such as a continuum scale, a gauge or a bar graph, a trend line, a pie chart, or a colorimetric scale, a digital scale, etc. The indication may also be tactile or auditory. The visual indication illustrates the quality of a VF in real time and allows the user to quickly assess the status and trajectory of the cardiac rhythm, allowing, for example, the CPR to continue as long as the quality of the cardiac rhythm, such as VF, is improving. One skilled in the art will realize that there are many ways of displaying an analog value. The examples shown here are graphical, but it is possible that numbers could be displayed as well, or combinations of numbers and graphics. The Shock Index value could be displayed, or the probability of VF could be displayed, or some other numerical indicator that relates to the waveform. This approach is superior to doing CPR for a fixed period or until a fixed level of quality disregarding the actual individual real-time patient data and status. If, for example, the VF quality is observed as not improving, other interventions are engaged rather than a continued CPR.

If VF quality continues to improve, the rescuer continues CPR with a higher degree of confidence and without unnecessary stopping or pausing at a predetermined threshold as may be recommended by existing guidelines. If VF quality is not improving it is possible that CPR quality is poor and that the caregiver should change the depth, rate or other parameter. It is possible that optimal CPR depth and rate may vary from one individual to another. This approach allows CPR to be adjusted dynamically based on the results with a given patient. VF quality indications given to the user allow assessment of the current VF quality and of whether it is improving.

Figure 18:
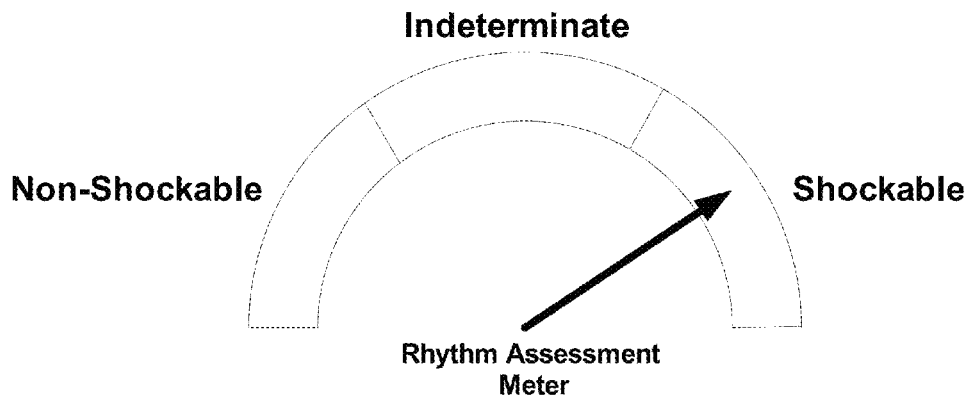
FIG. 18A is shock index probability, interpretation, and related recommended actions table.
FIG. 18B is an example of a rhythm assessment meter.
FIG. 18C is an example of a rhythm assessment meter.
Figure 18:
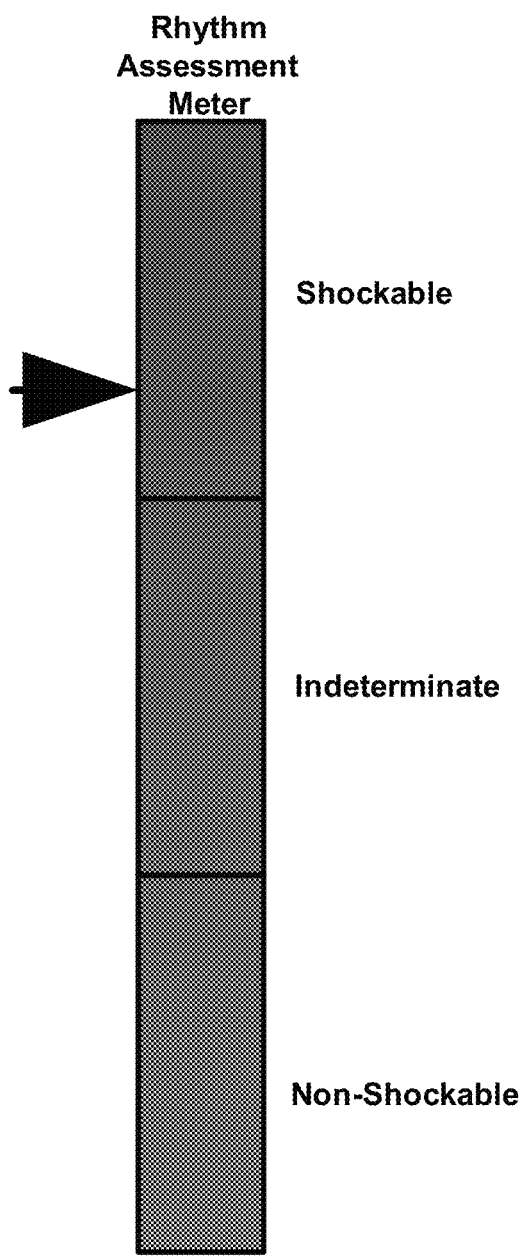

Further, FIGS. 18A-C illustrate embodiments of representations of shock recommendation using a logistic regression. The inputs for logical regression comprise numerical measurements of the ECG and impedance signals. The output of the logistic regression approach is a number such as a shock index number as illustrated in FIG. 18A. A positive shock index value indicates a shockable rhythm, a negative shock index indicates a non-shockable rhythm, and a value in the middle is indeterminate. A shock index value of zero means there is a 50-50 chance that the patient has VF. By way of an example, for "accuracy emphasis" mode all values between −2.5 and +2.5 are considered indeterminate; shockable rhythms are >2.5, non-shockable rhythms are <−2.5. Such analog meter, as illustrated in FIGS. 18B and 18C, exemplifies a "Rhythm Assessment Meter" and is, for example, displayed on a manual defibrillator screen. The far left of the meter scale is −5, the far right is +5, and the indeterminate zone goes from −2.5 to +2.5.

Figure 19:
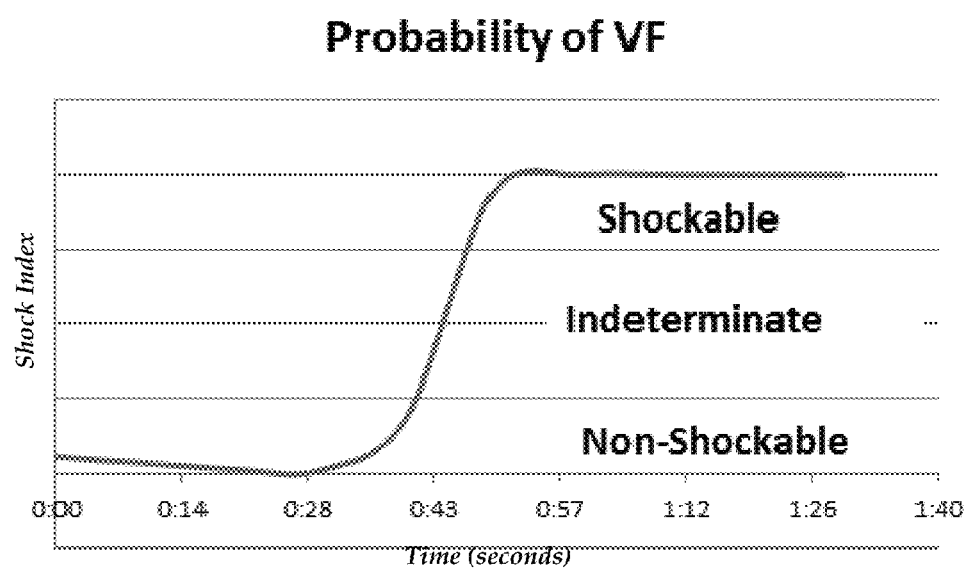
FIG. 19 is a time diagram of a VF probability.

FIG. 19 is an example of waveform assessment trend line. Here, the probability of VF in a patient starts at time $T_{0:00}$ with a non-shockable rhythm, and then transitions to a shockable rhythm after approximately 43 seconds of CPR. The trend line illustrates the probability of VF (as shown in FIG. 19), the shock index, or another numerical value relating to the patient waveform. The trend line illustrates the regions that should be considered shockable, non-shockable, and indeterminate, as presented in FIG. 17. The trend line illustrates when an individual is refibrillated and how long he/she had been in fibrillation. Also, if the trend line is steadily in the shockable or non-shockable zone, then the operator's confidence increases as to correctness of the rhythm analysis, whereas a number that is not consistently displaying is an indicator of uncertainty. The shock index can be calculated continuously, continually or at discrete intervals. The intervals could be based on the CPR interval, on the artifact level on the signal, the Central Processing Unit (CPU) burden for calculation, and/or other parameters. There may also be intervals during which no data is available.

When analyzing a noisy signal, like an ECG during CPR, it is not always possible to make a definitive interpretation. Providing an analog scale to the user conveys not only the recommendation, but the confidence level that is associated with that recommendation. A value far into a treatment zone, either shockable or non-shockable, is associated with a far greater confidence than a value near a boundary. Part of the value of the analog scale is that some users may make treatment decisions at a different confidence level than other users. If the artifact still cannot be filtered and/or the artifact levels are somehow excessive, persistent, or the signal contains noise, automatic analysis may indicate a different course of action and shift to a backup process or sequence.

In one embodiment, "blind" shocks are given to pulseless patients without assessing the rhythm. The understanding in the field is that the harm to the patient from an unnecessary shock is low in comparison to the harm to the patient from withholding a necessary shock. Rescuers, therefore, are disinclined to stop CPR to assess the rhythm, and choose to proceed with "blind" shocks. The present disclosure enables rescuers to monitor, in real time, what is the next most advantageous step he/she should take for the optimal benefit of the patient within certain confidence level.

A large sudden change on the rhythm assessment meter may indicate the onset of VF, while a small change may simply be the result of remaining, unfiltered noise. The device is further capable of voice prompts, flashing lights, signals, etc. when a certain zone with a certain confidence level is reached. The meter can further facilitate answers when an operator does not trust a filtered ECG signal. The meter is most valuable when an operator/rescuer has no way of knowing whether to trust the filtered ECG signal and when resuscitation needs to stop CPR to obtain a clean signal.

By way of an example, when the meter is in the indeterminate zone, the waveform may not be trusted. If the meter is in the shockable zone, the filtered waveform display may be helpful by providing an indication of the VF amplitude, a feature that provides an indication of the health of the patient. If the meter is in the non-shockable zone the rescuer may find it useful to know whether the patient is in asystole or pulseless electrical activity (PEA). If the patient appears to have regular, normal-rate QRS complexes the rescuer may choose to stop CPR to check for a pulse. Conversely, if they are confident that no QRS complexes are present they may choose to skip their normal pulse check.

Figure 20:
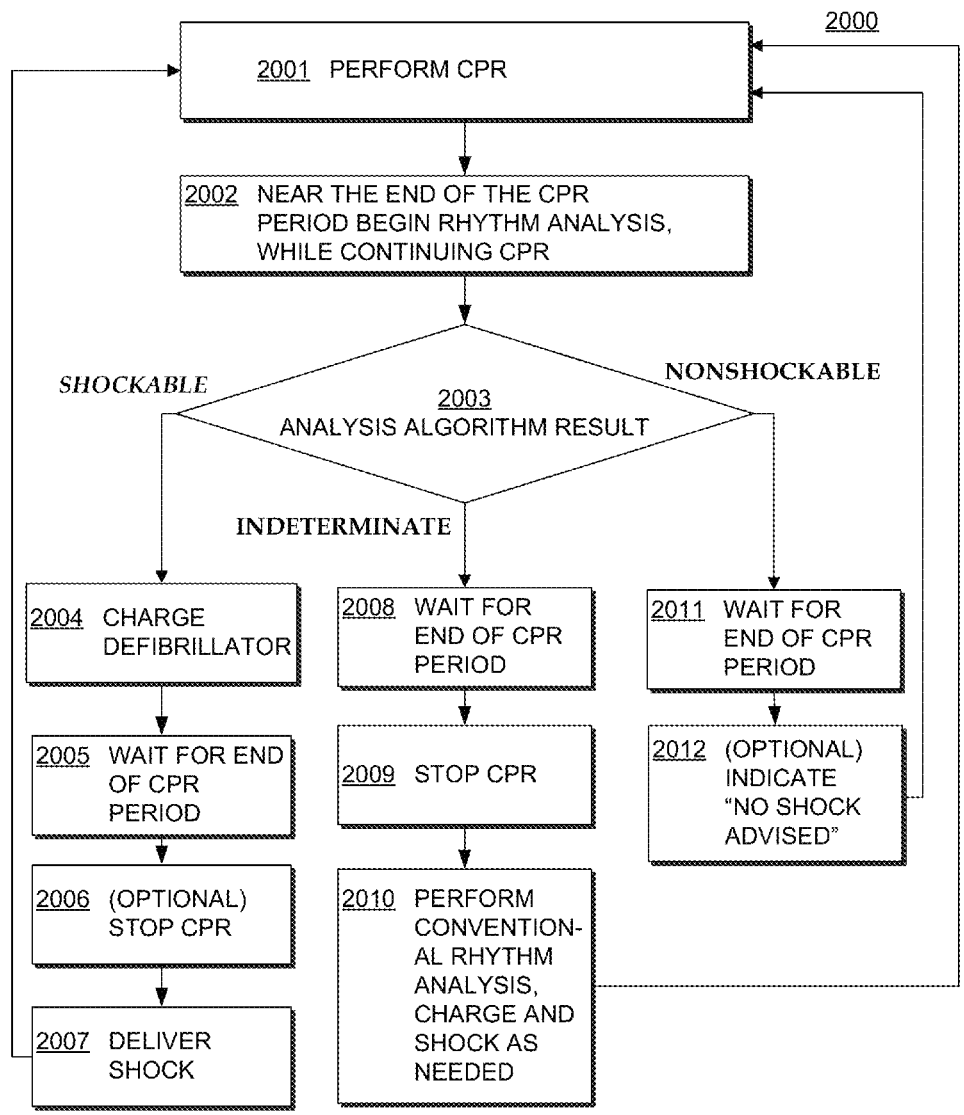
FIG. 20 is a flowchart for illustrating methods according to embodiments.
Figure 21:
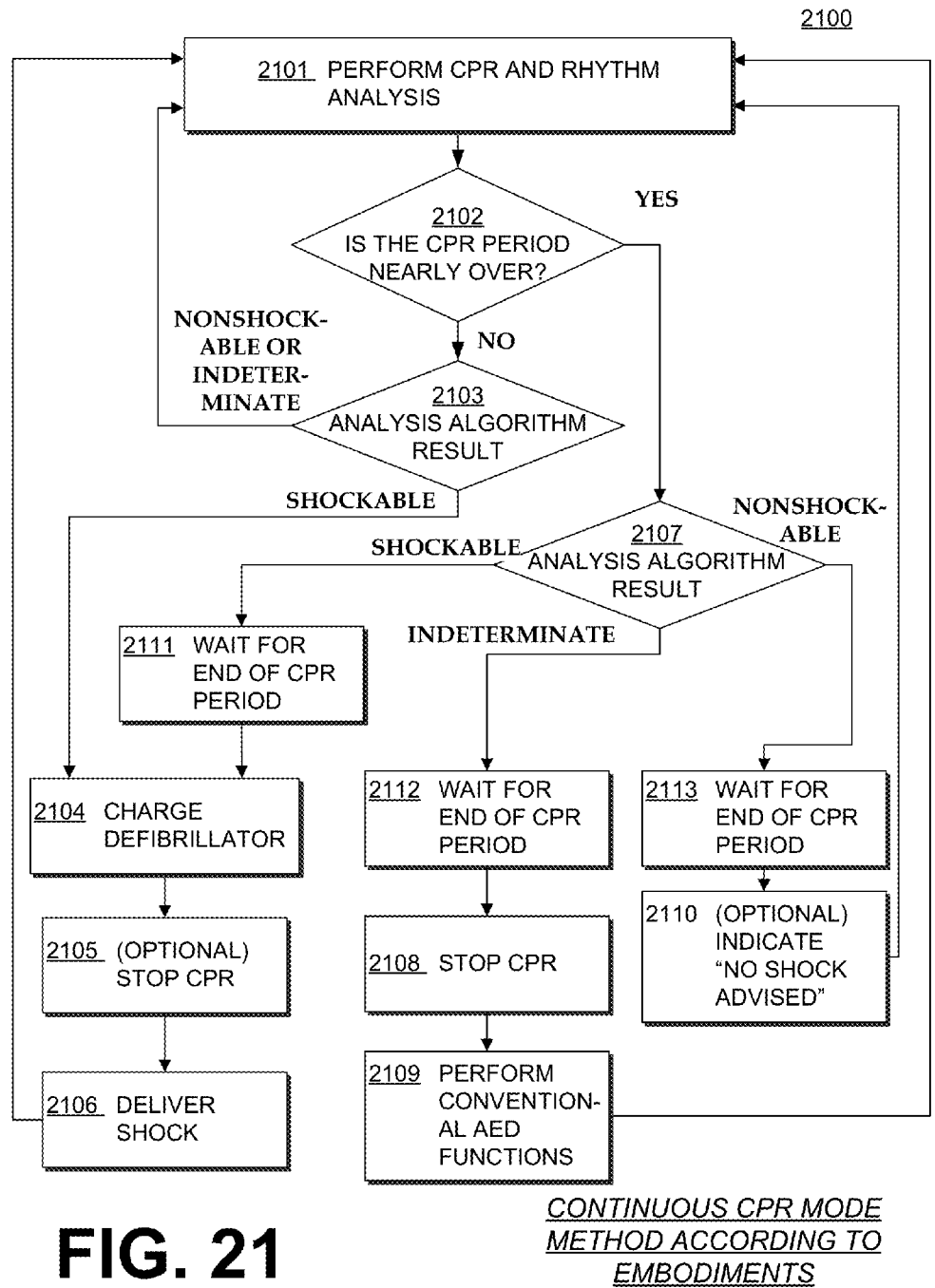
FIG. 21 is a flowchart for illustrating methods according to embodiments.
Figure 22:
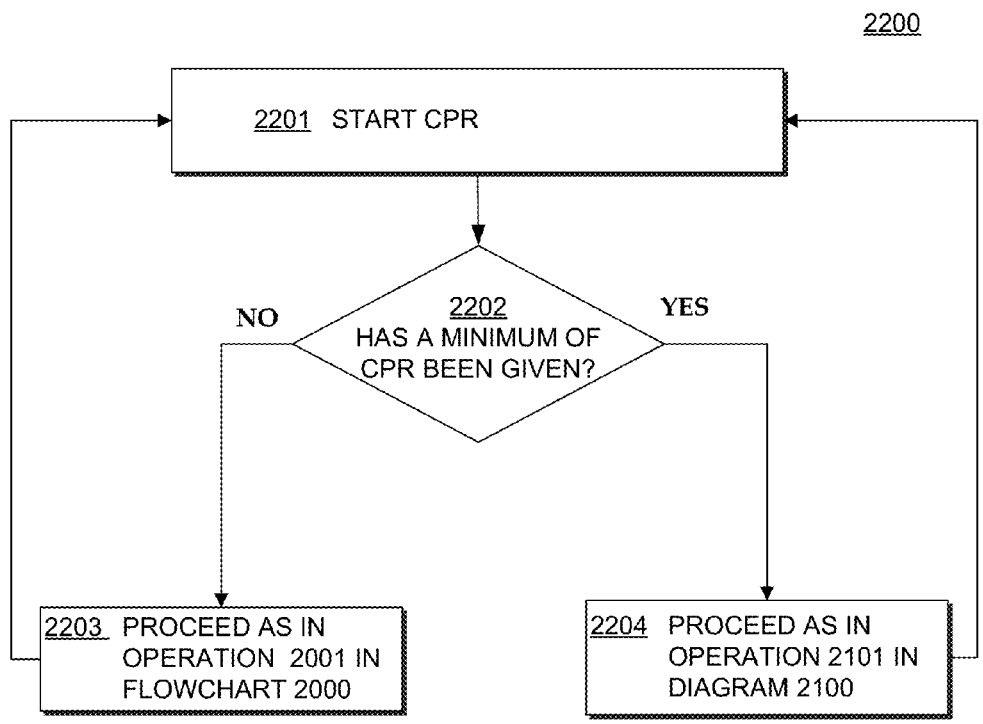
FIG. 22 is a flowchart for illustrating methods according to embodiments.

Integration of Cardiac Rhythm Analysis During CPR into a Defibrillator Algorithm In a further embodiment, a defibrillator, such as an AED, integrates a CPR prompting sequence. FIGS. 20, 21 and 22 illustrate steps for flexibly incorporating CPR prompting sequence into another device such as a defibrillator. In one embodiment, an AED user or a remote device is prompted to setup or flexibly adjust with setup options. Setup options can be decided upon, by way of an example, by a Medical Director of the person operating the defibrillator to conform to the treatment protocol he or she orders for all persons operating under his or her directorship. As such, the device can have provision to store the elected setup options so that the device prompts according to the ordered treatment protocol and/or algorithm. Memory storage may be made by nonvolatile memory, flash memory, disk memory or similar device, in other devices and communicated to the device by a wired or wireless communication channel, including the Internet. Other options are possible.

FIGS. 20, 21 and 22 detail the three general options, termed herein Periodic Mode, Continuous Mode and Minimum CPR Time, starting with prompts in 2001 2101 or 2201, respectively, according to the choice made by the Medical Director, for example. The prompting may start after the device is turned on, or following additionally an analysis without CPR or following additionally an Initial CPR period.

FIG. 20 is a flowchart illustrating the method 2000 for prompting and interacting with the analysis algorithm if Periodic Mode has been chosen. According to operation 2001 the user is prompted to perform CPR. According to an operation at 2002 the rhythm analysis begins, silently in the preferred embodiment. This begins toward the end of the CPR period. The amount of time before the end of the CPR period to begin the rhythm analysis is determined by the time it will take various operations to take place such that the device is ready to shock at the end of the CPR period without pause. This will be determined by such factors as the amount of data necessary for rhythm analysis and the time necessary to acquire that data, the computation time of the algorithm, and the time necessary to charge the defibrillator.

According to a decision step at 2003 the result of the analysis algorithm determines the operations subsequently taken.

If the analysis algorithm determination is shockable, according to an operation at 2004 the defibrillator is charged.

According to a next operation at 2005 the device waits until the end of the CPR period. This might be necessary, for example, if the time it takes to perform various operations before operation 2005 is variable, and the longest possible must be taken into account in operation 2002. Alternatively, the device could prompt for shock delivery as soon as the charging is complete.

Optionally, according to an operation at 2006, the user is prompted to stop CPR. This might not be necessary if it is possible to safely shock while doing CPR, as would be the case with a mechanical CPR device or when the rescuer performing CPR is wearing gloves or other barrier to prevent being shocked.

According to a next operation at 2007, the shock is delivered. It may be delivered with or without pressing a shock switch.

If the analysis algorithm determination is indeterminate, according to an operation at 2008, the device waits until the end of the CPR period.

According to an operation at 2009, the user is then prompted to stop CPR.

According to an operation at 2010, the device then performs a rhythm analysis using an algorithm which is appropriate for patients who are not receiving CPR, as is common in the state of the art.

If the analysis algorithm determination is nonshockable, according to an operation at 2011, the device waits until the end of the CPR period.

Optionally, according to an operation at 2012, the algorithm indicates to the user that no shock is advised.

No matter the analysis algorithm result at an operation 2003, processing proceeds to the operation at 2001.

FIG. 21 is a flowchart 2100 for illustrating the method of prompting and interacting with the analysis algorithm if Continuous Mode has been chosen. According to operation 2101 the user is prompted to perform CPR and the rhythm analysis starts at the same time. The rhythm analysis is silent in the preferred embodiment.

According to a decision step at 2102 the flowchart the result of the analysis algorithm determines the operations subsequently taken. The CPR period is nearly over if the amount of time before the end of the CPR period is such that the device will be ready to shock at the end of the CPR period without pause. This will be determined by such factors as the amount of data necessary for rhythm analysis and the time necessary to acquire that data, the computation time of the algorithm and the time necessary to charge the defibrillator.

According to a decision step at 2103 the result of the analysis algorithm determines the operations subsequently taken.

If the result of the analysis algorithm is no or indeterminate, the device continues the CPR period and continuous to perform the rhythm analysis according to decision step 2101.

If the analysis algorithm determination is shockable, according to an operation at 2104 the defibrillator is charged.

Optionally, according to an operation at 2105, the user is prompted to stop CPR. This might not be necessary if it is possible to safety shock while doing CPR, as would be the case with a mechanical CPR device or when the rescuer performing CPR is wearing gloves or other barrier to prevent being shocked.

According to a next operation at 2106, the shock is delivered. It may be delivered with or without pressing a shock switch. Unlike Periodic Mode, this occurs as soon as the rhythm is determined to be shockable no matter how much of the CPR period has completed.

If the decision step at 2102 is that the CPR period is nearly over, then according a decision step at 2107, the subsequent operation steps are determined by the analysis algorithm result, but in a different fashion than is outlined in decision step 2103. It is possible that the algorithm works slightly or completely differently in step 2107 than in 2103. For example, there may be an advantage to a different tradeoff between sensitivity and specificity in the algorithm because the impact to the patient of an incorrect nonshockable result in processing step 2103 is for the user to perform more CPR, but in processing step 2107 it would result in failure to deliver therapy to a patient who needed it.

If the analysis algorithm determination in step 2107 is indeterminate, according to an operation at 2108, the user is then prompted to stop CPR.

According to an operation at 2009, the device then performs a rhythm analysis using an algorithm which is appropriate for patients who are not receiving CPR, as is common in the state of the art.

If the analysis algorithm determination is nonshockable, optionally, according to an operation at 2012, the algorithm indicates to the user that no shock is advised.

No matter the analysis algorithm result at an operation 2103 or 2107, processing proceeds to the operation at 2101.

FIG. 22 is a flowchart 2200 for illustrating the method of prompting and interacting with the analysis algorithm if Minimum CPR Time has been chosen. This option is like Continuous Mode as illustrated in FIG. 21, but ensures that the patient receives a minimum amount of CPR.

According to an operation 2201 the user is prompted to perform CPR.

According to a decision step at 2202 the result of the analysis algorithm determines the operations subsequently taken. The step tests to see if a minimum amount of CPR has been given. The amount of CPR can be determined by either the duration of one CPR period or by separate input from the Medical Director or by some equivalent means.

If the minimum amount of CPR has not been given, according to an operation at 2203 operation proceeds as outlined in operation 2001 in flowchart 2000. If the minimum amount of CPR has been given, according to an operation at 2204 operation proceeds as outlined in operation 2101 in flowchart 2100.

In a further embodiment the system and method for electrocardiogram analysis for optimization of chest compressions and therapy and delivery include the rhythm assessment meter device and the filtered waveform display where the meter and the display complement and corroborate results of one another and the system arms a rescuer/operator with results based on a certain confidence level. For example, the waveform changes its appearance when the rhythm assessment meter is in the indeterminate zone. In another example, if the waveform can not be trusted, the waveform changes to a specific color, gray—for example, or perhaps to a dashed line. Alternatively, a visual or audible indication is given when the filtered waveform provides low confidence level to the rescuer.

Figure 23:
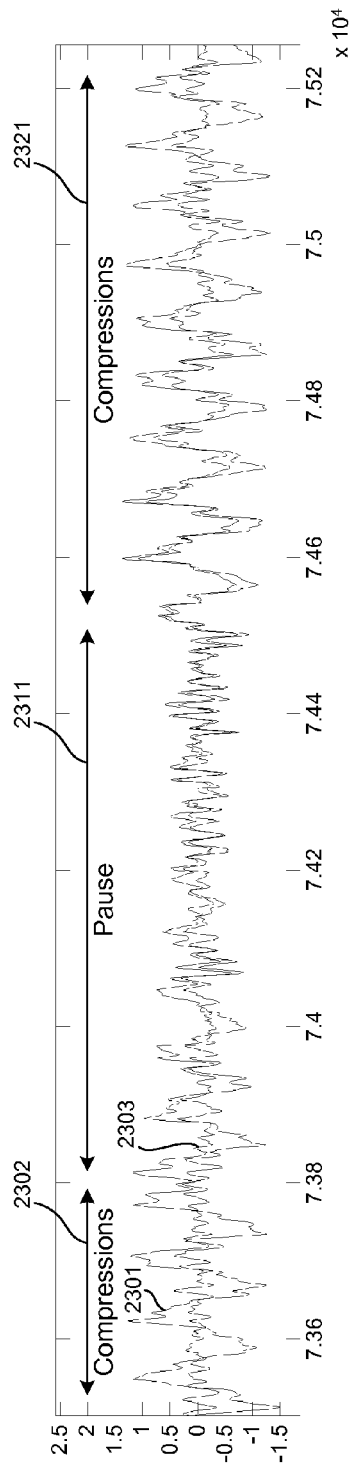
FIG. 23 is a time diagram showing unfiltered and filtered ECG signals during CPR with a pause, according to embodiments.

In FIG. 23, the signal 2301 represents the ECG signal taken from a cardiac arrest patient who was receiving mechanical chest compressions with a pause. The signal 2303 is same signal that has been filtered with at least one filter mechanism (not shown) comprising a comb filter, such as an embodiment of the filter mechanism 425 described above. In this embodiment, at least one filter mechanism is implemented using an IIR filter, which incorporates a "memory" that takes time to respond to changes in the ECG signal 2301.

During a compressions period 2302, the start of the ECG signal 2301 shows a significant amount of compression artifact that would interfere with rhythm interpretation. The at least one filter mechanism has removed compression artifact in a portion of the ECG signal 2301 during the compressions period 2302. This filtering revealed that the patient is experiencing VF (ventricular fibrillation), as shown in a portion of the filtered signal 2303 during the compressions period 2302. As can be seen, that portion of the ECG signal 2301 is noisy and that portion of the filtered signal 2303 is relatively clean during the compressions period 2302.

During a pause period 2311 (i.e., when compressions are paused) the situation is reversed—a portion of the ECG signal 2301 is relatively clean and a portion of the filtered signal 2303 contains artifact. Due to the nature of the IIR filter used in this embodiment of at least one filter mechanism, the amount of artifact on that portion of the filtered signal 2303 diminishes over time during the pause period 2311. This delay in reducing the artifact can be problematic for EMS rescuers who may be used to rapidly assessing the patient's rhythm during a compression pause. This behavior of the at least one filter mechanism (i.e., injecting artifact during a compression pause) is inherent in a comb filter structure and may also occur with other filters such as notch filters and adaptive filters.

After compressions restart in a compressions period 2321, there is artifact on both the ECG signal 2301 and the filtered signal 2303. Over time the at least one filter mechanism "re-learns" the shape of the artifact, but the response delay can be undesirable. Pause periods such as the pause period 2311 can occur when the rescuer stops and restarts the compression device. Pause periods may also happen periodically if the device is programmed to include automatic ventilation pauses in a pattern such as a 30:2 compression/ventilation ratio. The artifact that would be inserted during a compression pause could be annoying to rescuers because they may be looking at the ECG during a pause. In this situation the at least one filter mechanism may not perform as they would likely expect—the at least one filter mechanism removes the artifact during the compressions and inserts it during an early portion of a CPR pause.

Figure 24:
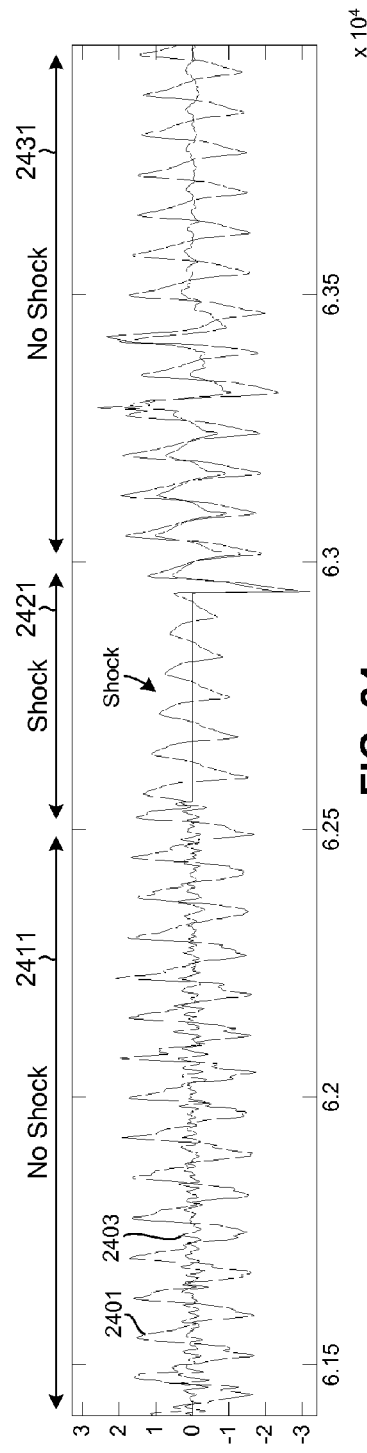
FIG. 24 is a time diagram showing unfiltered and filtered ECG signals during CPR with a shock, according to embodiments.

In FIG. 24, the signal 2401 represents the ECG signal taken from the same cardiac arrest patient who was receiving mechanical chest compressions at a different time period in which a defibrillation shock was delivered to the patient. The signal 2403 is same signal that has been filtered with the at least one filter mechanism (not shown). During a non-shock period 2411, a portion of the ECG signal 2401 shows compression artifact and a portion of the filtered signal 2403 shows the ECG signal with the artifact removed.

During a time period 2421, a defibrillation shock is delivered to the patient. No ECG data is available during the shock, so a portion of the ECG signal 2401 is represented as a flat line in the period 2421. During the time period 2421, a portion of the filtered signal 2403 has some compression artifact because the at least one filter mechanism must "re-learn" the artifact.

In a post shock time period 2431, eventually the at least one filter mechanism learns the artifact and begins to show a cleaned-up signal later in the time period 2431, but the delay can be undesirable in some applications. Filter delays such as this are particularly undesirable after a defibrillation shock because they interfere with the ability of rescuers to determine whether the shock succeeded and deciding whether another shock may be necessary.

The examples shown above use a comb filter for the purposes of illustration, similar problems are likely to be observed with any IIR filter or FIR filter with a long memory. Similarly, adaptive filters may take time to respond to signal changes. In general, any filtering technique that has a "learning" aspect may experience similar problems.

Further, there may be other types of disturbances that can cause similar artifacts as the at least one filter mechanism relearns the artifact. Various embodiments described below can be used to detect these disturbances.

In one embodiment, a monitoring device (e.g., a monitor) is aware of events such as a monitoring lead falling off or a change in the monitoring lead vector. This information is communicated to the monitoring device so that appropriate compensation can be provided as will be described below. For example, in some embodiments, the information is provided to the at least one filter mechanism so that it Scan make the appropriate compensation. If the monitor is an external defibrillator, then the at least one filter mechanism can also be configured to compensate for shock disturbances.

In other embodiments, pauses in compressions can be detected by the monitoring device using signal analysis of the ECG signal. For example, mechanical compressions have a very specific frequency signature. The absence of that signature could be taken as evidence that the compressions have stopped. Another method of detecting mechanical compressions is to run an inverse comb filter and detect the amplitude of the resulting signal. Both of these techniques may take time to acquire enough data and may be appropriate in less time urgent applications.

In other embodiments, pauses in compressions can be detected by the monitoring device using the impedance signal if it is available. One method of detecting the presence of compressions is to take the RMS value of the impedance signal over a 600 ms period. If the RMS value is above a threshold then it is likely that compressions are occurring. This method may have less delay than ECG signal analysis, but also may be less specific. Other types of motion may affect the RMS value, causing erroneous detection of compressions.

In still other embodiments, the CPR machine can communicate with the monitoring device when compressions are going to be started or stopped. The monitoring device can then compensate for the disturbance. In one particular embodiment, the CPR machine would provide advance notice that compressions are going to be started or stopped so that the monitoring device can compensate before the memory of the at least one filtering mechanism is disturbed.

In yet another embodiment, the monitoring device may be able to anticipate some signal disturbances simply by knowing what kind of CPR machine that is being used. For example, some CPR machines may provide precisely-controlled timing for a 30:2 compression/ventilation ratio. The monitoring device may then anticipate the ventilation pause simply based on the elapsed time since the last known pause (e.g., detecting using the ECG or impedance signal). This method is particularly advantageous because it requires no communication between the CPR machine and the monitoring device but still allows the pause locations to be precisely identified.

In response to detecting a disturbance (e.g., via any of the various embodiments described above), the monitoring device is configured to selectively compensate for the detected disturbance. Various embodiments described below can be used to provide the compensation.

In one embodiment, once a pause in compressions is identified the monitoring device can choose to automatically switch from displaying the filtered signal to displaying the unfiltered signal. This would avoid the problem seen in FIG. 23 in which the filtered signal has more artifact than the original ECG signal during a compression pause. However, when compressions are restarted the at least one filtering mechanism still needs to re-learn the artifact.

In another embodiment, after a disturbance it is possible to make the at least one filtering mechanism learn more quickly by temporarily reducing the quality factor (i.e. the "Q") of the at least one filtering mechanism. Note, quality factor of the at least one filtering mechanism is described above in conjunction with FIG. 7. In one embodiment, the at least one filtering mechanism implemented using a comb filter has a relatively high Q value of 16. The Q of the comb filter can be changed relatively easily by changing the value of "b" in the comb filter transfer function. For example, the Q could be reduced to a value of 2 for one second after a disturbance, and then switched back to 16. This would allow the filter to recover relatively quickly when compressions are started, a monitoring lead is attached, or after a shock has been delivered.

In still another embodiment, the disturbance to the filtered ECG signal is reduced by controlling the CPR machine to restart the compressions after a pause in a manner in which the new compression group is in-phase with the previous compression group. For example, if the compression rate is 100 compressions per minute, each compression requires 0.6 seconds. If compression pauses are arranged to be an integer number of 0.6 second intervals, then the new compression group will be in-phase with the previous compression group. This reduces the amount of re-learning that the at least one filtering mechanism needs to do.

In yet another embodiment, if the CPR machine restarts compressions in-phase with the previous compression group and the monitoring device knows where the compression pause starts and ends, then it is possible for the monitor device to "protect" the at least one filtering mechanism during the pause. This would allow the at least filtering mechanism to retain its memory of the artifact during the pause rather than "unlearning." Then, when compressions are restarted the at least one filtering mechanism could be re-engaged without having to relearn the artifact again. This would avoid a significant disturbance of the filter for every compression pause.

One method of protecting the at least one filter mechanism during a pause is simply to stop the at least one filtering mechanism (i.e. prevent it from accepting any new inputs, prevent it from shifting the delay lines, and prevent it from calculating any new outputs). Then the at least one filtering mechanism is restarted at the appropriate time when compressions are resumed. The at least one filtering mechanism is restarted at substantially the same point in the compression cycle as it stopped. As described above, this could be done if there was communication between the CPR machine and the monitor device, or if the monitoring device had advance knowledge of the length of the compression pause.

Figure 25:
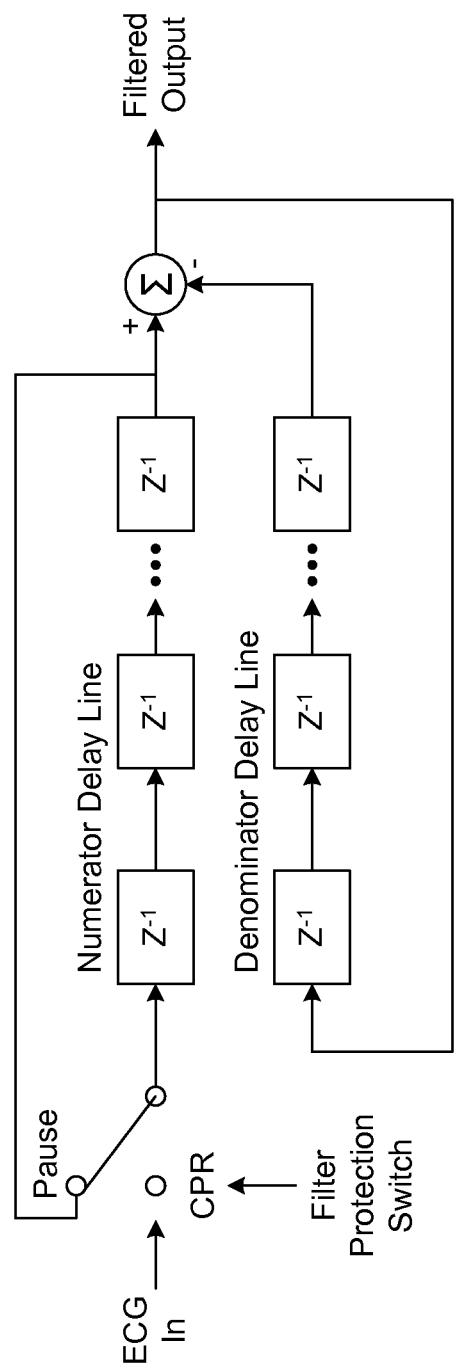
FIG. 25 is an example block diagram of a filter mechanism with a protection switch according to embodiments.

FIG. 25 shows one embodiment of a filter mechanism 2500 with a protection switch 2502. The switch 2502 allows the filter mechanism 2500 to operate normally during chest compressions but to transition to a protected mode during a pause. In the protected mode the input to the numerator delay line is taken from the output of the numerator delay line is rather than the input signal. This recirculates the existing data (which contains compression artifact) through the filter mechanism 2500 during a pause, which prevents the unlearning effect. When compressions are restarted the input to the numerator delay line is switched back to the input ECG and the filter mechanism 2500 begins removing the CPR artifact without having to relearn the artifact shape.

This method has the advantage that the filter mechanism 2500 could be restarted at any point in the compression cycle and the filter would still be in sync with the artifact.

In another embodiment, the at least one filter mechanism is protected during a compression pause by changing the Q of the filter. A filter with a high Q learns the new signal very slowly. If the Q of the filter was made extremely high during a compression pause it is possible that little or no new learning would happen during the pause. If the Q was switched back to the normal value when compressions are restarted the filter would still be in sync with the artifact and the need for learning would be avoided. A similar technique could be used with an adaptive filter that avoids relearning during compression pauses.

In this description, numerous details have been set forth in order to provide a thorough understanding. In other instances, well-known features have not been described in detail in order to not obscure unnecessarily the description. A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. For instance, the mechanical chest compression devices described above may operate at different frequencies than those described above, have different tolerance thresholds than those described above, have different harmonics than those described above, or any combination thereof. Indeed, the frequencies, tolerances, harmonics, and any other variables or values pertinent to the disclosed technology that are discussed or otherwise presented herein are provided only as certain examples. Modifications to the disclosed technology can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. A system for treating a cardiac arrest patient, the system comprising:
    an ECG monitor; and
    a mechanical chest compression device wherein,
        the mechanical chest compression device is configured to automatically deliver a series of chest compressions and ventilation pauses,
        the ECG monitor is configured to filter the ECG signal to remove the compression artifact and produce a filtered ECG signal, and
        the ECG monitor is configured to display the filtered signal when the mechanical chest compression device is delivering chest compressions and displays the unfiltered ECG signal during ventilation pauses, wherein the ECG monitor includes a filter configured to perform the filtering of the ECG signal by attenuating a plurality of regularly spaced bands, and wherein the ECG monitor is configured to change a quality factor (Q) of the filter responsive to an event.

2. The system of claim 1, wherein the ECG monitor is configured to identify the ventilation pauses.

3. The system of claim 2, wherein the ECG monitor is further configured to automatically switch from displaying the filtered ECG signal to displaying the unfiltered ECG signal responsive to identifying the ventilation pauses.

4. The system of claim 1, wherein the mechanical chest compression device is configured to transmit a signal to the ECG monitor indicative of the ventilation pauses.

5. The system of claim 1, wherein the filter comprises a comb filter.

6. The system of claim 1, wherein the event includes an attachment of a monitoring lead to the ECG monitor, a delivery of a shock, or a beginning of the delivery of chest compressions.

7. The system of claim 1, wherein the ECG monitor is configured to temporarily reduce the Q of the filter from a first value to a second value responsive to the event.

8. The system of claim 7, wherein the ECG monitor is further configured to restore the Q of the filter from the second value back to the first value after a period of time.

9. The system of claim 7, wherein the period of time is one second.

10. The system of claim 7, wherein the first value is 16.

11. The system of claim 7, wherein the second value is 2.

12. A system for treating a cardiac arrest patient, the system comprising:
    an ECG monitor; and
    a mechanical chest compression device wherein,
        the mechanical chest compression device is configured to automatically deliver a series of chest compressions and ventilation pauses,
        the ECG monitor is configured to filter the ECG signal to remove the compression artifact and produce a filtered ECG signal, and
        the ECG monitor is configured to display the filtered signal when the mechanical chest compression device is delivering chest compressions and displays the unfiltered ECG signal during ventilation pauses, wherein the ECG monitor includes a filter configured to perform the filtering of the ECG signal by attenuating a plurality of regularly spaced bands, and wherein the ECG monitor includes a filter protection switch configured to allow the filter to operate normally during the chest compressions.

13. The system of claim 12, wherein an input to a numerator delay line of the filter is the ECG signal.

14. The system of claim 12, wherein the filter protection switch is further configured to switch to a protected mode during the ventilation pauses.

15. The system of claim 14, wherein an input to a numerator delay line of the filter is taken from an output of the numerator delay line when the filter protection switch is in the protected mode.

16. The system of claim 15, wherein the filter protection switch is further configured to switch back from the protected mode to allow the filter to operate normally again responsive to a resuming of the chest compressions after the ventilation pauses.

17. The system of claim 16, wherein the input to the numerator delay line of the filter is the ECG signal when the filter protection switch is no longer in the protected mode.

18. The system of claim 12, wherein the filter comprises a comb filter.

19. The system of claim 12, wherein the ECG monitor is configured to identify the ventilation pauses.

20. The system of claim 19, wherein the ECG monitor is further configured to automatically switch from displaying the filtered ECG signal to displaying the unfiltered ECG signal responsive to identifying the ventilation pauses.

21. The system of claim 12, wherein the mechanical chest compression device is configured to transmit a signal to the ECG monitor indicative of the ventilation pauses.

\* \* \* \* \*